United States Patent [19]

Fujimoto et al.

[11] 4,205,170
[45] May 27, 1980

[54] PROPIONIC ACID DERIVATIVES

[75] Inventors: Yasuo Fujimoto, Tokyo; Shigeru Yamabe, Kobe, both of Japan

[73] Assignee: Nippon Chemiphar Company, Limited, Tokyo, Japan

[21] Appl. No.: 855,076

[22] Filed: Nov. 28, 1977

[30] Foreign Application Priority Data

Dec. 3, 1976 [JP] Japan .................................. 51-145403
Dec. 3, 1976 [JP] Japan .................................. 51-145404
Jun. 17, 1977 [JP] Japan .................................. 52-71690

[51] Int. Cl.² .................. C07D 491/04; C07D 495/04; C07D 313/14; C07D 337/14
[52] U.S. Cl. ...................................... 546/80; 424/256; 424/275; 424/278; 546/89; 260/333; 549/12
[58] Field of Search ................ 260/294.8 B, 295–297, 260/327 B, 333; 546/80, 89

[56] References Cited

U.S. PATENT DOCUMENTS 3,931,205   1/1976   Nakanishi et al. ............... 260/295 T

FOREIGN PATENT DOCUMENTS 2442979   3/1975   Fed. Rep. of Germany ....... 260/327 B
52-53876  4/1977   Japan ......................................... 549/12
1475950   6/1977   United Kingdom ....................... 549/12

*Primary Examiner*—Natalie Trousof
*Attorney, Agent, or Firm*—Oblon, Fisher, Spivak, McClelland & Maier

[57] ABSTRACT

Propionic acid derivatives having the formula

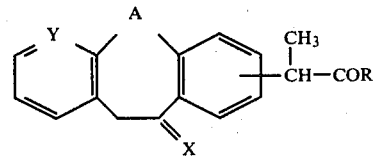

wherein X represents an oxygen or two hydrogen atoms, Y represents CH or N, A represents an oxygen or sulfur atom, and R represents hydroxy, amino, or a lower alkoxy group having 1 to 5 carbon atoms are antiinflammatory agents.

44 Claims, No Drawings

PROPIONIC ACID DERIVATIVES

This invention relates to novel propionic acid derivatives and to a process for producing the same.

The present inventors have examined a wide variety of compounds and, as a result found that the propionic acid derivatives of formula (I);

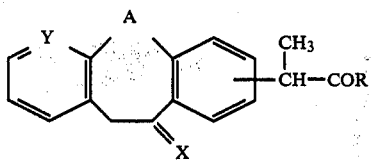
(I)

wherein X represents an oxygen or two hydrogen atoms, Y represents CH or N, A represents an oxygen or sulfur atom, and R represents hydroxy, amino or a lower alkoxy group having 1 to 5 carbon atoms, possess an excellent antiinflammatory action.

It is, therefore, one object of this invention to provide a novel propionic acid derivative represented by formula (I).

It is another object of this invention to provide a propionic acid derivative of formula (I) possessing a strong antiinflammatory action.

It is a further object of this invention to provide a novel process for producing the propionic acid derivatives of formula (I).

The compounds of the formula (I) are divided into following groups having formulae (II) and (III);

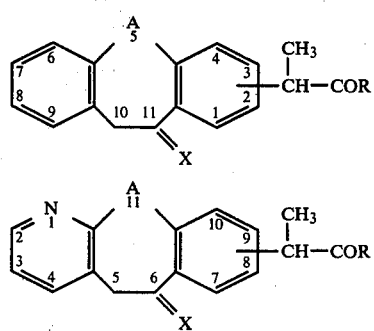

wherein A, X and R are the same as defined above.

In the compounds (II) and (III), the group represented by the formula —CH(CH₃)COR can be substituted at any one of the 2-, 3- or 4- positions of formula (II), and at any one of the 8-, 9- or 10- positions of formula (III).

The compounds of the formulae (II) and (III) are further divided into the following groups of the formulae (IV) and (V); and (VI) and (VII), respectively.

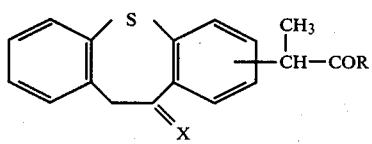
(IV)

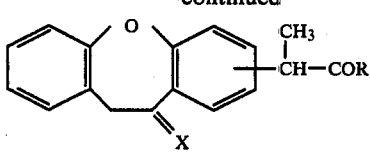
(V)

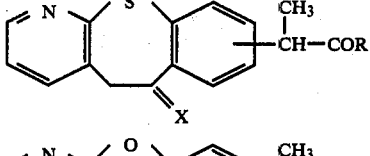
(VI)

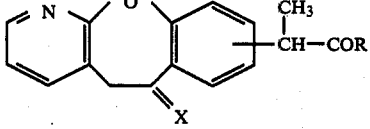
(VIII)

wherein X and R are same as defined above.

The compounds of formula (IV) are subdivided into the following groups of formulae (VIII) and (IX),

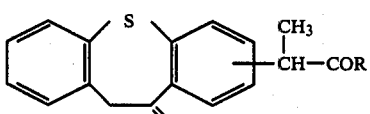
(VIII)

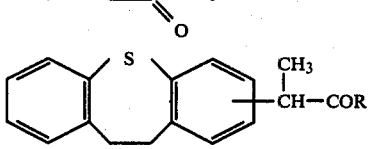
(IX)

wherein R is the same as defined above.

The compounds of formula (V) are subdivided into the following groups of formulae (X) and (XI),

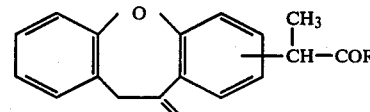
(X)

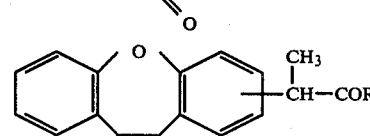
(XI)

wherein R is the same as defined above.

The compounds of formula (VI) are subdivided into the following groups of formulae (XII) and (XIII),

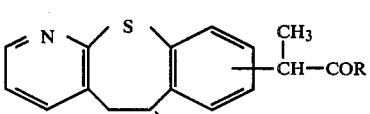
(XII)

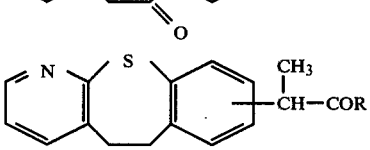
(XIII)

wherein R is the same as defined above.

The compounds of formula (VII) are subdivided into the following groups of formulae (XIV) and (XV),

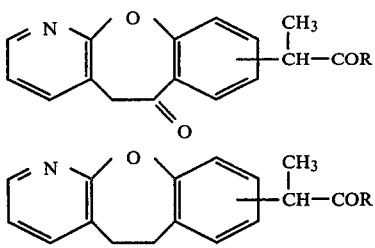

wherein R is the same as defined above.

The compounds of formulae (VIII) to (XV) are further subdivided based on the position of the substituent —CH(CH₃)COR. Of the compounds of formula (I) preferred are the compounds of formulae (VIII), (X), (XIII) and (XV).

Of the above compounds particularly preferred are the compounds represented by formulae (XVI) to (XIX),

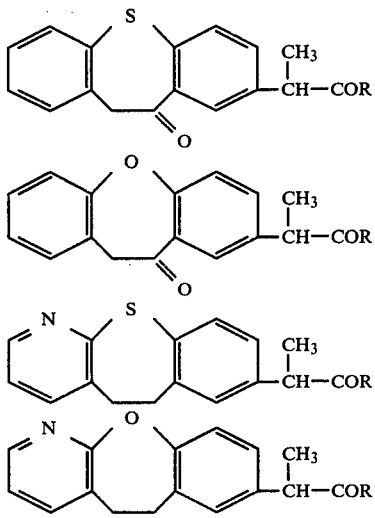

wherein R is the same as defined above.

According to the present invention, the compounds of formula (I) are produced by any one of the processes shown below.

PROCESS 1

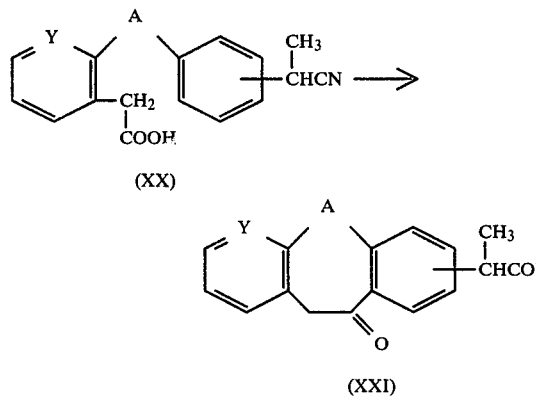

wherein Y and A are the same as defined above.

According to process 1, the compounds of formula (XXI) are produced by cyclizing the compounds of formula (XX) or active derivatives thereof in the presence of a condensing agent.

Suitable condensing agents to be used include, for example, polyphosphoric acid, polyphosphoric acid ester and the like. The reaction is preferably conducted for 0.5 to 4 hours at 80 to 150° C. with or without a solvent.

The starting materials of formula (XX) are produced according to the following scheme;

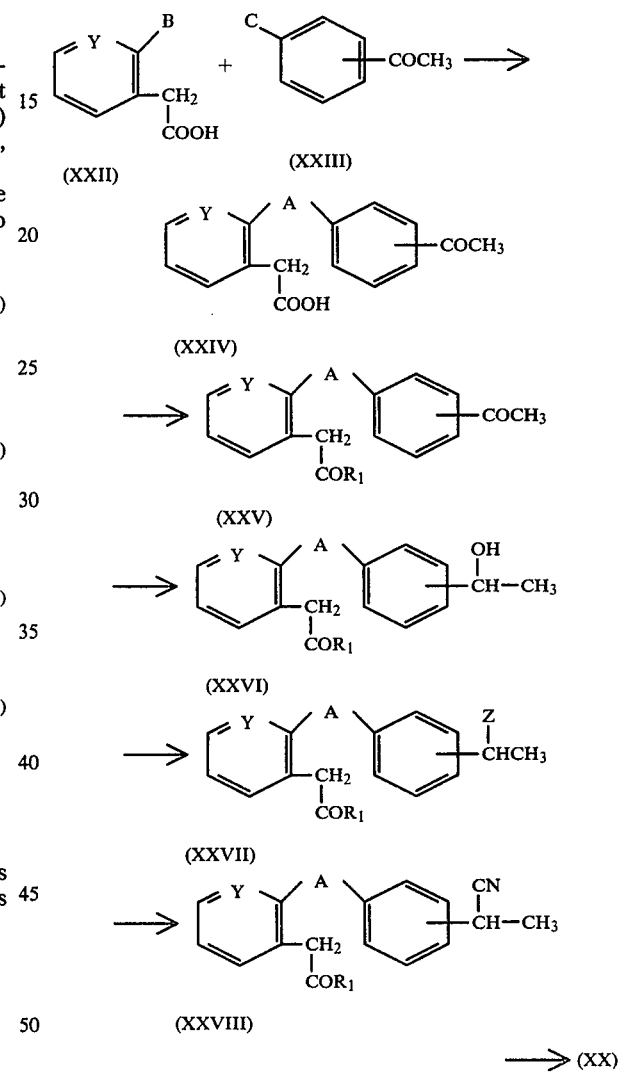

wherein Y and A are the same as defined above, R₁ represents a lower alkoxy group having 1 to 5 carbon atoms, B and C represent a halogen atom, hydroxy or mercapto group or a metallic salt thereof wherein B is a halogen atom when C is a hydroxy or mercapto group or a metallic salt thereof, and B is a hydroxy or mercapto group or a metallic salt thereof when C is a halogen atom, and Z represents a halogen atom.

That is, the compounds of formula (XXII) are reacted with the acetophenone derivatives of formula (XXIII) to produce the compounds of formula (XXIV), which are esterified with a lower alcohol to produce the compounds of formula (XXV), which are reduced to produce the compounds of formula (XXVI), which are halogenated to produce the compounds of formula (XXVII), which are reacted with a metallic cyanide to produce the compounds of formula (XXVIII), which are hydrolyzed, and thus are obtained the compounds of the formula (XX).

Alternatively, the compounds of formula (XXV) may be produced by reacting a lower alkyl ester of the compounds of formula (XXII) with the compounds of formula (XXIII).

PROCESS 2

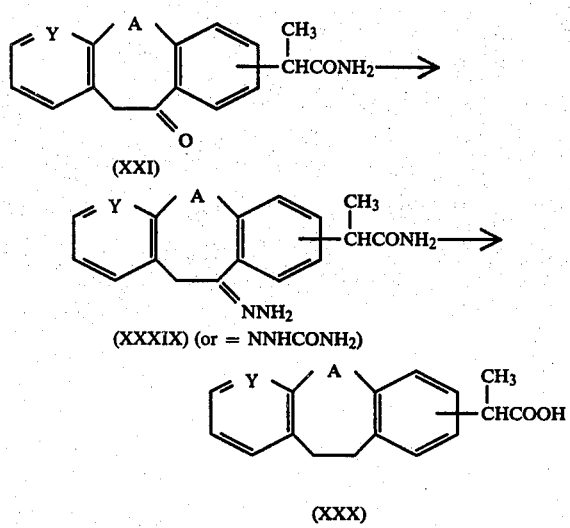

wherein Y and A are the same as defined above.

According to process 2, the compounds of formula (XXX) are produced by reacting the compounds of formula (XXI) with hydrazine or semicarbazide and reacting the resulting hydrazone or semicarbazone of formula (XXIX) with an alkaline agent.

In producing the compounds of the formula (XXIX) from compounds of formula (XXI), the reaction may be conducted without solvent, but is preferably conducted in an organic solvent, for example, alcohols such as methanol and ethanol; and ethers such as dioxane and tetrahydrofuran for 1 to 8 hours under reflux conditions.

In producing the compounds of formula (XXX) from the compounds of formula (XXIX), the compounds of formula (XXIX) are reacted with an alkaline agent in an inert solvent which does not participate in the reaction, for example, alcohols such as ethanol, t-butanol and diethyleneglycol; and ethers such as dioxane and tetrahydrofuran, preferably in diethyleneglycol at 100° to 200° C. for 1 to 5 hours.

Alkaline agents to be used in this reaction include potassium hydroxide, sodium hydroxide and metallic alkoxides.

PROCESS 3

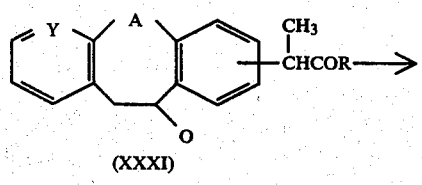

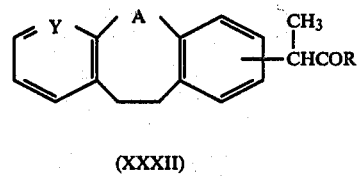

wherein Y, A and R are the same as defined above.

According to process 3, the compounds of formula (XXXII) are produced by reducing the compounds of formula (XXXI), preferably by a Clemmensen reduction. The reaction is preferably conducted in an inert solvent, containing a small amount of conc. hydrochloric acid and water in the presence of zinc or zinc-amalgam for 1 to 4 hours under reflux conditions.

PROCESS 4

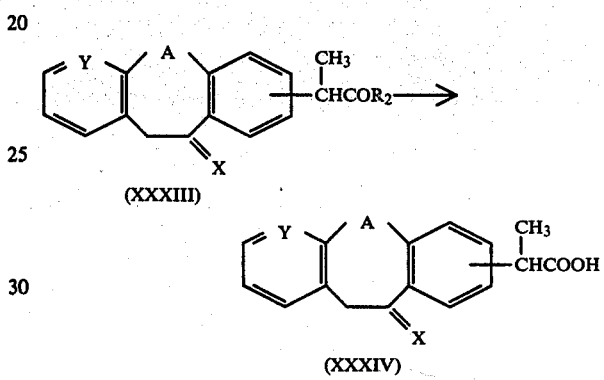

wherein Y, A and X are the same as defined above, and $R_2$ represents amino or a lower alkoxy group having 1 to 5 carbon atoms.

This reaction is carried out by the usual method. That is, the reaction is preferably conducted in a solvent containing some water, for example, an alcohol such as methanol or ethanol containing a small amount of water with the use of a catalyst such as potassium hydroxide, sodium hydroxide, hydrochloric acid or sulfuric acid at temperatures from room temperature to the boiling point of the solvent.

PROCESS 5

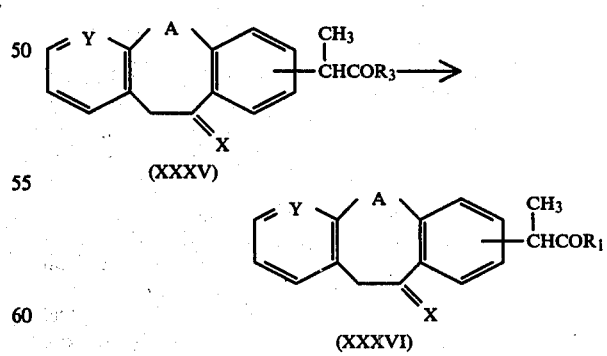

wherein X, Y and A are the same as defined above, $R_1$ represents a lower alkoxy group having 1 to 5 carbon atoms and $R_3$ represents a hydroxy or amino group.

This reaction is carried out by the usual method. That is, the reaction is preferably conducted in an alcohol $R_1H$ (wherein $R_1$ is the same as defined above) with the use of a mineral acid such as sulfuric acid or hydrochloric acid at temperatures from room temperature to the boiling point of the solvent for 1 to 5 hours.

PROCESS 6

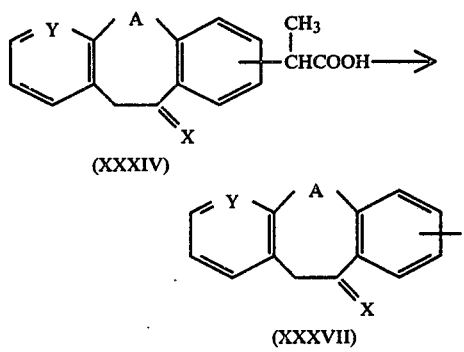

wherein X, Y and A are the same as defined above.

In producing the compounds of formula (XXXVII) from the compounds of formula (XXXIV), diazomethane is preferably used. That is, to a solution of the compounds of formula (XXXIV) is added diazomethane dissolved in diethyl ether and the mixture is stirred at room temperature, whereby there are obtained the compounds of formula (XXXVII) in good yield

PROCESS 7

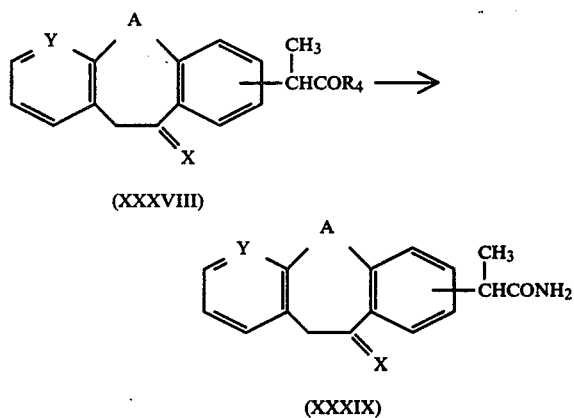

wherein X, Y and A are the same as defined above and $R_4$ represents hydroxy or a lower alkoxy group having 1 to 5 carbon atoms.

According to process 7, the compounds of formula (XXXVIII), acid halides thereof, mixed acid anhydrides thereof or an activated ester thereof are reacted with ammonia in a solvent which does not participate in the reaction, for example, methylene chloride, benzene, toluene or chloroform at room temperature or under reflux conditions. When free propionic acid derivatives of formula (XXXIV) are used, a condensing agent, such as dicyclohexyl carbodiimide may be used.

The compounds of this invention exhibit both oral and parenteral activity and can be formulated in dosage forms for oral, parenteral, rectal, or topical administration. Solid dosage forms for oral administration include capsules, tablets, pills, powders, and granules. In such solid dosage forms, the active compound is admixed with at least one inert diluent such as sucrose, lactose, or starch. Such dosage forms can also comprise, as is normal practice, additional substances other than inert diluent, e.g., lubricating agents such as magnesium stearate. In the case of capsules, tablets, and pills, the dosage forms may be also comprise buffering agents. Tablets and pills can additionally be prepared with an enteric coating.

Liquid dosage forms for oral administration include pharmaceutically acceptable emulsions, solution, suspensions, syrups, and elixirs containing inert diluents commonly used in the art, such as purified water and alcohols. Besides inert diluents, such compositions can also include adjuvants, such as wetting agents, emulsifying and suspending agents, and sweetening, flavoring, and perfuming agents. Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyl oleate.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.4 to 20 mg/Kg of body weight daily are administered to mammals to obtain effective relief of inflammation.

The compounds of the present invention represented by the formula (I) possess excellent antiinflammatory effects.

That is, male Wistar rats weighing about 100 g, one group consisting of 5 to 7 animals, were given orally the compounds according to the present invention and then edema was induced in the hind paws by subcutaneous injections of 0.1 ml of 1% carrageenan 1 hour after the administration of the test compounds, and the volumes of the hind paws were measured by a volume differential meter. The results obtained are shown in Table 1.

Table 1

| Test Compounds | Dose mg/kg | Inhibition (%) | | | | | |
|---|---|---|---|---|---|---|---|
| | | 1 hr | 2 hr | 3 hr | 4 hr | 5 hr | 6 hr |
| Compound 1 | 10 | 47.1 | 66.7 | 70.5 | 73.6 | 68.0 | 66.0 |
| 2 | 10 | 55.0 | 76.3 | 78.0 | 78.5 | 74.8 | 70.0 |
| 2 | 1 | 53.8 | 57.3 | 70.9 | 69.6 | 68.7 | 65.6 |
| 3 | 10 | 62.3 | 72.0 | 79.9 | 78.2 | 74.5 | 64.5 |
| 4 | 10 | 47.2 | 58.8 | 54.6 | 48.3 | 41.0 | 35.0 |
| 5 | 10 | 56.6 | 68.0 | 67.4 | 52.2 | 38.7 | 29.3 |
| 6 | 10 | 65.9 | 41.5 | 31.8 | 26.1 | 22.3 | 20.5 |
| 7 | 10 | 58.7 | 39.6 | 31.2 | 25.9 | 22.3 | 18.8 |
| 8 | 10 | 43.2 | 37.8 | 26.9 | 20.1 | 15.8 | 15.1 |
| 9 | 10 | 52.1 | 41.0 | 27.5 | 21.3 | 16.6 | 16.3 |
| 10 | 10 | 71.2 | 69.3 | 76.3 | 76.7 | 56.4 | 34.4 |
| 11 | 10 | 21.2 | 56.8 | 64.9 | 70.0 | 62.8 | 52.6 |
| 12 | 10 | 34.2 | 58.3 | 79.4 | 83.1 | 71.1 | 51.4 |
| 13 | 10 | 42.4 | 55.5 | 65.4 | 63.3 | 49.1 | 33.3 |
| 14 | 10 | 48.6 | 67.6 | 60.3 | 53.2 | 35.8 | 26.0 |
| 15 | 10 | 36.1 | 44.1 | 53.3 | 48.7 | 33.0 | 27.2 |
| 16 | 10 | 53.6 | 49.9 | 50.7 | 46.2 | 37.0 | 26.2 |
| 17 | 10 | 65.9 | 49.4 | 35.4 | 29.0 | 17.2 | 13.0 |
| 18 | 8 | 34.3 | 36.4 | 38.3 | 36.1 | 36.1 | 35.1 |
| 19 | 10 | 45.1 | 51.3 | 28.2 | 25.1 | 18.7 | 10.2 |
| 20 | 10 | 45.0 | 54.3 | 47.5 | 33.8 | 28.9 | 24.3 |
| 21 | 10 | 69.5 | 75.6 | 69.0 | 67.0 | 70.3 | 64.6 |
| 22 | 10 | 29.6 | 51.7 | 59.1 | 57.0 | 45.9 | 42.8 |
| 23 | 5 | 22.6 | 53.8 | 60.9 | 64.1 | 51.8 | 37.5 |
| 24 | 10 | 19.6 | 52.1 | 49.9 | 38.3 | 28.2 | 27.2 |

Table 1-continued

| Test Compounds | Dose mg/kg | Inhibition (%) | | | | | |
|---|---|---|---|---|---|---|---|
| | | 1 hr | 2 hr | 3 hr | 4 hr | 5 hr | 6 hr |
| 25 | 10 | 42.8 | 57.7 | 61.0 | 52.7 | 33.4 | 29.2 |
| 26 | 5 | 55.7 | 52.6 | 40.0 | 32.2 | 29.7 | 24.0 |
| 27 | 5 | 68.0 | 83.5 | 79.0 | 81.0 | 70.6 | 61.5 |
| 28 | 5 | 11.7 | 35.1 | 50.9 | 55.4 | 47.1 | 37.7 |
| 29 | 5 | 18.1 | 38.3 | 53.5 | 53.8 | 46.2 | 42.9 |
| 30 | 5 | 21.4 | 56.4 | 59.0 | 52.8 | 38.6 | 27.3 |
| Phenyl butazone | 10 | 12.4 | 23.7 | 27.4 | 20.0 | 14.4 | 8.6 |
| " | 5 | — | 22.7 | 21.1 | 22.2 | 13.1 | 13.6 |
| Flufenamic acid | 10 | −2.9 | 23.9 | 26.8 | 29.5 | 23.8 | 15.4 |
| " | 5 | 6.8 | 25.9 | 26.2 | 25.3 | 16.0 | 10.6 |
| Indomethacin | 10 | 64.4 | 59.8 | 52.1 | 63.8 | 54.4 | 50.3 |
| " | 5 | 38.3 | 51.7 | 59.2 | 58.4 | 48.7 | 41.0 |
| " | 1 | 21.6 | 39.6 | 29.9 | 36.4 | 28.9 | 28.7 |

Compound
1: 2-(10,11-dihydro-11-oxodibenzo[b,f]thiepin-2-yl)-propionamide
2: 2-(10,11-dihydro-11-oxodibenzo[b,f]thiepin-2-yl)-propionic acid
3: Ethyl 2-(10,11-dihydro-11-oxodibenzo[b,f]thiepin-2-yl)-propionate
4: 2-(10,11-dihydrodibenzo[b,f]thiepin-2-yl)-propionic acid
5: Ethyl 2-(10,11-dihydrodibenzo[b,f]thiepin-2-yl)-propionate
6: 2-(10,11-dihydro-11-oxodibenzo[b,f]thiepin-3-yl)-propionic acid
7: Ethyl 2-(10,11-dihydro-11-oxodibenzo[b,f]thiepin-3-yl)-propionate
8: Ethyl 2-(10,11-dihydrodibenzo[b,f]thiepin-3-yl)-propionate
9: 2-(10,11-dihydrodibenzo[b,f]thiepin-3-yl)-propionic acid
10: 2-(10,11-dihydro-11-oxodibenzo[b,f]oxepin-2-yl)-propionamide
11: Ethyl 2-(10,11-dihydro-11-oxodibenzo[b,f]oxepin-2-yl)-propionate
12: 2-(10,11-dihydro-11-oxodibenzo[b,f]oxepin-2-yl)-propionic acid
13: 2-(10,11-dihydrodibenzo[b,f]oxepin-2-yl)-propionic acid
14: Ethyl 2-(10,11-dihydrodibenzo[b,f]oxepin-2-yl)-propionate
15: 2-(10,11-dihydrodibenzo[b,f]oxepin-2-yl)-propionamide
16: 2-(10,11-dihydro-11-oxodibenzo[b,f]oxepin-3-yl)-propionic acid
17: 2-(10,11-dihydro-11-oxodibenzo[b,f]oxepin-4-yl)-propionamide
18: 2-(10,11-dihydro-11-oxodibenzo[b,f]oxepin-4-yl)-propionic acid
19: 2-(10,11-dihydrodibenzo[b,f]oxepin-4-yl)-propionic acid
20: 2-(5,6-dihydro-6-oxobenzo[b]pyrido[3,2-f]thiepin-8-yl)-propionic acid
21: 2-(5,6-dihydrobenzo[b]pyrido[3,2-f]thiepin-8-yl)-propionic acid
22: Ethyl 2-(5,6-dihydrobenzo[b]pyrido[3,2-f]thiepin-8-yl)-propionate
23: 2-(5,6-dihydrobenzo[b]pyrido[3,2-f]thiepin-8-yl)-propionamide
24: 2-(5,6-dihydrobenzo[b]pyrido[3,2-f]thiepin-9yl)-propionic acid
25: Ethyl 2-(5,6-dihydrobenzo[b]pyrido[3,2-f]thiepin-9-yl)-propionate
26: 2-(5,6-dihydro-6-oxobenzo[b]pyrido[3,2-f]oxepin-8-yl)-propionic acid
27: 2-(5,6-dihydrobenzo[b]pyrido[3,2-f]oxepin-8yl)-propionic acid
28: Ethyl 2-(5,6-dihydrobenzo[b]pyrido[3,2-f]oxepin-8-(yl)-propionate
29: 2-(5,6-dihydrobenzo[b]pyrido[3,2-f]oxepin-8-yl)-propionamide
30: 2-(10,11-dihydrodibenzo[b,f]thiepin-2-yl)-propionamide As can be seen from the results of Table 1, the present compounds possess significant effects; in particular, the compounds represented by the formulae (XVI), (XVII), (XVIII) and (XIX) have excellent effects in comparison with Phenyl-butazone, Flufenamic acid and Indomethacin which are widely used as antiinflammatory drugs.

The invention is illustrated below in further detail with reference to Examples, but the invention is not limited to the Examples.

EXAMPLE 1

2-(10,11-dihydro-11-oxo dibenzo[b,f]thiepin-2-yl)-propionamide.

To 289 mg of 2-[4′-(α-cyanoethyl)-phenylthio]-phenylacetic acid was added 5.8 g of polyphosphoric acid and the mixture was stirred at 100° C. for 30 minutes. To this was added ice-water and the mixture was extracted with ethyl acetate and the extract was washed with saturated sodium hydrogencarbonate solution, then saturated sodium chloride solution, and dried over anhydrous sodium sulfate. The solvent was distilled off to obtain 207 mg of pale brown oil, which was chromatographed over silica gel, and eluted with n-hexane/acetone(3/1). There was obtained 110 mg of 2-(10,11-dihydro-11-oxo dibenzo[b,f]thiepin-2-yl)-propionamide as pale yellow crystals having a melting point of 180.8°–184.8° C. These were recrystallized from acetone/n-hexane to give crystals having a melting point of 190.0°–192.5° C.

IR($\nu_{max}^{KBr}$cm$^{-1}$): 3530, 3420 (NH$_2$), 1660 (C=O).
NMR(CDCl$_3$)δ: 1.42 (3H,d,J=8Hz,=CH-C$\underline{H}_3$); 3.52 (1H,q,J=8Hz,=C$\underline{H}$-CH$_3$); 4.28 (2H,s,—CH$_2$—CO—); 5.30–5.82 (2H,broad,—CON$\underline{H}_2$); 7.0–7.64 (6H,m,aromatic protons); 8.01 (1H,s,C$_1$—$\underline{H}$).

EXAMPLE 2

2-(10,11-dihydro-11-oxo dibenzo[b,f]thiepin-2-yl)-propionic acid.

To 105 mg of 2-(10,11-dihydro-11-oxo dibenzo[b,f]thiepin-2-yl)-propionamide were added 150 mg of potassium hydroxide, 1 ml of ethanol and 1 ml of water, and the resulting mixture was refluxed for 6 hours. After cooling, to this was added water and the mixture was extracted with ethyl acetate. The aqueous layer was acidified with hydrochloric acid, extracted with ethyl acetate and the extract was washed with saturated sodium chloride solution and dried over anhydrous sodium sulfate. The solvent was distilled off to obtain reddish brown oil, which was chromatographed over silica gel, and eluted with n-hexane/acetone (15/2). There was obtained 45 mg of pale yellow oil which was crystallized from n-hexane to give 28 mg of 2-(10,11-dihydro-11-oxo dibenzo[b,f]thiepin-2-yl)-propionic acid as white crystals having a melting point of 141°–146° C. A part of the crystals was further recrystallized from benzene/n-hexane to give crystals having a melting point of 155°–156.5° C.

IR($\nu_{max}^{KBr}$cm$^{-1}$): 1710, 1675 (C=O).

NMR(CDCl$_3$)δ: 1.39 (3H,d,J=8Hz,=CHC$\underline{H}_3$); 3.62 (1H,q,J=8Hz,=C$\underline{H}$CH$_3$); 4.22 (2H,s,—CO—C$\underline{H}_2$—); 6.89-7.53 (6H,m,aromatic protons); 7.95 (1H,d,J=2Hz,C$_1$—$\underline{H}$); 9.81-10.09 (1H,b.s,—COO$\underline{H}$).

EXAMPLE 3 ethyl 2-(10,11-dihydro-11-oxo dibenzo[b,f]thiepin-2-yl)-propionate.

To 200 mg of 2-(10,11-dihydro-11-oxo dibenzo[b,f]-thiepin-2-yl)-propionamide in 4 ml of ethanol was added 0.4 ml of conc. sulfuric acid and the mixture was refluxed with stirring for 1 hour. The solvent was distilled off to obtain the residue, to which was added pieces of ice, and the mixture was extracted with ethyl acetate and the extract was washed with saturated sodium hydrogen carbonate, then saturated sodium chloride solution and dried over anhydrous sodium sulfate. The solvent was distilled off to obtain brown oil, which was chromatographed over silica gel, and eluted with benzene-chloroform. There was obtained 141 mg of ethyl 2-(10,11-dihydro-11-oxo dibenzo[b,f]-thiepin-2-yl)-propionate as pale yellow oil.

IR($\nu_{max}^{KBr}$cm$^{-1}$): 1730, 1680 (C=O).

NMR(CDCl$_3$)δ: 1.06 (3H,t,J=7Hz,—CH$_2$C$\underline{H}_3$); 1.34 (3H,d,J=7Hz,=CHC$\underline{H}_3$); 3.58 (1H,q,J=7Hz,=C$\underline{H}$CH$_3$); 3.98 (2H,q,J=7Hz,—CH$_2$C$\underline{H}_3$); 4.23 (2H,s,—COCH$_2$—); 6.96-7.70 (6H,m,aromatic protons); 8.02 (1H,d,J=2Hz,C$_1$—$\underline{H}$).

MS(m/e): 326 (M+).

EXAMPLE 4

2-(10,11-dihydro-11-hydrazo dibenzo[b,f]thiepin-2-yl)-propionamide.

To 30 mg of 2-(10,11-dihydro-11-oxo dibenzo[b,f]-thiepin-2-yl)-propionamide in 2 ml of ethanol was added 0.3 ml of hydrazine hydrate and the mixture was refluxed for 2 hours. After cooling, the solvent was distilled off to obtain the residue, which was extracted with chloroform and the extract was washed with saturated sodium chloride solution and dried over anhydrous sodium sulfate. The solvent was distilled off to give 32 mg of 2-(10,11-dihydro-11-hydrazo dibenzo[b,f]thiepin-2-yl)-propionamide as yellow crystals.

IR($\nu_{max}^{KBr}$cm$^{-1}$): 3400-3100 (NH$_2$), 1660 (C=O).
MS(m/e): 311 (M+).

EXAMPLE 5

2-(10,11-dihydro dibenzo[b,f]thiepin-2-yl)-propionic acid.

The mixture of 32 mg of 2-(10,11-dihydro-11-hydrazo dibenzo[b,f]thiepin-2-yl)-propionamide, 800 mg of potassium hydroxide and 8 ml of diethylene glycol was stirred at 150° C. for 1.5 hours. After cooling, to this was added water and the mixture was acidified with hydrochloric acid, extracted with ethyl acetate and the extract was washed with saturated sodium chloride solution and dried over anhydrous sodium sulfate. The solvent was distilled off to obtain brown oil, which was subjected to thin layer chromatography to obtain 10 mg of 2-(10,11-dihydro dibenzo[b,f]thiepin-2-yl)-propionic acid as pale yellow oil. This was crystallized from benzene-n-hexane to give colorless crystals having a melting point of 103°-104.5° C.

IR($\nu_{max}^{KBr}$cm$^{-1}$): 1705 (C=O). MS(m/e): 284 (M+)

EXAMPLE 6 ethyl 2-(10,11-dihydro dibenzo[b,f]thiepin-2-yl)-propionate.

To 100 mg of 2-(10,11-dihydro dibenzo[b,f]thiepin-2-yl)-propionic acid was added 2 ml of ethanol containing 17% of hydrogen chloride and the mixture was stirred at room temperature for 3 hours. The solvent was distilled off to obtain the residue, to which was added ice-water and extracted with ethyl acetate, and the extract was washed with saturated sodium chloride solution and dried over anhydrous sodium sulfate. The solvent was distilled off to obtain pale brown oil, which was chromatographed over silica gel and eluted with benzene-chloroform. There was obtained 96 mg of ethyl 2-(10,11-dihydro dibenzo[b,f]thiepin-2-yl)-propionate as pale yellow oil.

IR($\nu_{max}^{KBr}$cm$^{-1}$): 1730 (C=O).

NMR(CDCl$_3$)δ: 1.16 (3H,t,J=7Hz,—CH$_2$C$\underline{H}_3$); 1.43 (3H,d,J=7Hz,=CHC$\underline{H}_3$); 3.28 (4H,s,—C$\underline{H}_2$C$\underline{H}_2$—); 3.60 (1H,q,J=7Hz,=C$\underline{H}$CH$_3$); 4.07 (2H,q,J=7Hz,—C$\underline{H}_2$CH$_3$); 6.80-7.50 (7H,m,aromatic protons);

MS (M/e): 312 (M+).

EXAMPLE 7

2-(10,11-dihydro dibenzo[b,f]thiepin-2-yl)-propionamide.

An amount of 55 mg of 2-(10,11-dihydro dibenzo[b,f]-thiepin-2-yl)-propionic acid was dissolved in 0.5 ml of chloroform solution containing 0.02 ml of triethylamine and the resulting mixture was added dropwise with ice-cooling over a period of 5 minutes to 0.5 ml of chloroform solution containing 0.02 ml of ethyl chlorocarbonate. The mixture was stirred for 10 minutes at the same temperature, then at room temperature for 30 minutes after introduction of ammonia gas. After the completion of the reaction, to this was added water and the resulting mixture was extracted with chloroform. The extract was washed with dilute sodium hydroxide solution, then saturated sodium chloride solution, and dried over anhydrous sodium sulfate. The solvent was distilled off to obtain pale brown crystals, which were chromatographed over silica gel, eluted with chloroform, and there were obtained pale yellow crystals. These were recrystallized from benzene-n-hexane to give 26 mg of 2-(10,11-dihydro dibenzo[b,f]thiepin-2-yl)-propionamide as colorless crystals having a melting point of 135°-135.5° C.

IR($\nu_{max}^{KBr}$cm$^{-1}$): 3380, 3180 (NH$_2$), 1650 (C=O).

NMR(CDCl$_3$)δ: 1.47 (3H,d,J=7Hz,=CHC$\underline{H}_3$); 3.32 (4H,s,—C$\underline{H}_2$C$\underline{H}_2$—); 3.49 (1H,q,J=7Hz,=C$\underline{H}$CH$_3$); 5.34 (2H,b.s,—CON$\underline{H}_2$); 6.80-7.60 (7H,m,aromatic protons).

MS(m/e): 283 (M+).

EXAMPLE 8

2-(10,11-dihydro-11-oxo dibenzo[b,f]thiepin-3-yl)-propionamide.

To 1.8 g of 2-[3'-(α-cyanoethyl)-phenylthio]-phenylacetic acid was added 36 g of polyphosphoric acid and the mixture was stirred at 100° to 105° C. for 1 hour. After cooling, to this was added ice-water and the resulting mixture was extracted with ethyl acetate. The extract was washed with saturated sodium carbonate solution, then saturated sodium chloride solution, and dried over anhydrous sodium sulfate. The solvent was distilled off to obtain 1.64 g of pale brown oil, which was chromatographed over silica gel, eluted with n-hexane/acetone(5/1–1/1), and there were obtained 990 mg of 2-(10,11-dihydro-11-oxo dibenzo[b,f]thiepin-3-yl)-propionamide as pale orange crystals. These were recrystallized from acetone to give pale yellow crystals having a melting point of 178°–179° C.

IR($\nu_{max}^{KBr}$cm$^{-1}$): 3350 (CONH$_2$), 1680 (C=O).

NMR(CDCl$_3$)$\delta$: 1.50 (3H,d,J=7Hz,=CHC$\underline{H}_3$); 3.57 (1H,q,J=7Hz,=C$\underline{H}$CH$_3$); 4.32 (2H,s,—CO—C$\underline{H}_2$—); 5.24–5.82 (2H,b.s,CON$\underline{H}_2$); 7.02–7.72 (6H,m,aromatic protons); 8.12 (1H,d,J=8Hz,C$_1$—$\underline{H}$).

EXAMPLE 9

2-(10,11-dihydro-11-oxo dibenzo[b,f]thiepin-3-yl)-propionic acid.

To 250 mg of 2-(10,11-dihydro-11-oxo dibenzo[b,f]thiepin-3-yl)-propionamide were added 3 ml of ethanol, 400 mg of potassium hydroxide and 2 ml of water and the mixture was refluxed with stirring for 4.5 hours. After cooling, the solvent was distilled off to obtain the residue, to which was added 1N-sodium hydroxide solution and the mixture was extracted with ethyl acetate. The aqueous layer was acidified with hydrochloric acid and extracted with ethyl acetate. This extract was washed with saturated sodium chloride solution and dried over anhydrous sodium sulfate. The solvent was distilled off to obtain 250 mg of pale brown oil, which was chromatographed over silica gel and there was obtained 117 mg of 2-(10,11-dihydro-11-oxo dibenzo[b,f]thiepin-3-yl)-propionic acid as pale yellow oil.

IR($\nu_{max}^{CHCl_3}$cm$^{-1}$): 1715, 1675 (C=O).

NMR(CDCl$_3$)$\delta$: 1.50 (3H,d,J=7Hz,=CHC$\underline{H}_3$); 3.76 (1H,q,J=7Hz,=C$\underline{H}$CH$_3$); 4.30 (2H,s,—CO—C$\underline{H}_2$—); 7.02–7.65 (6H,m,aromatic protons); 8.12 (1H,d,J=8Hz,C$_1$—$\underline{H}$); 8.87 (1H,b.s,COO$\underline{H}$).

MS(m/e): 298 (M+).

EXAMPLE 10 ethyl 2-(10,11-dihydro-11-oxo dibenzo[b,f]thiepin-3-yl)-propionate.

To 300 mg of 2-(10,11-dihydro-11-oxo dibenzo[b,f]thiepin-3-yl)-propionamide in 3 ml of ethanol was added 0.3 ml of conc. sulfuric acid and the mixture was refluxed for 3.5 hours. The solvent was distilled off to obtain the residue, to which was added pieces of ice, and the mixture was extracted with ethyl acetate. The extract was washed with saturated sodium chloride solution and dried over anhydrous sodium sulfate. The solvent was distilled off to obtain brown oil, which was chromatographed over silica gel, eluted with chloroform, and there was obtained 277 mg of ethyl 2-(10,11-dihydro-11-oxo dibenzo[b,f]thiepin-3-yl)-propionate as pale brown oil.

IR($\nu^{maxCHCl_3}$cm$^{-1}$): 1730, 1675 (C=O).

NMR(CDCl$_3$)$\delta$: 1.10 (3H,t,J=7Hz,—CH$_2$C$\underline{H}_3$); 1.48 (3H,d,J=7Hz,=CHC$\underline{H}_3$); 3.66 (1H,q,J=7Hz,=C$\underline{H}$CH$_3$); 4.08 (2H,q,J=7Hz,—C$\underline{H}_2$CH$_3$); 4.30 (2H,s—CO—C$\underline{H}_2$—); 7.00–7.66 (6H,m,aromatic protons); 8.08 (1H,d,J=8Hz,C$_1$—$\underline{H}$).

EXAMPLE 11 ethyl 2-(10,11-dihydro dibenzo[b,f]thiepin-3-yl)-propionate

To 172 mg of ethyl 2-(10,11-dihydro-11-oxo dibenzo[b,f]-thiepin-3-yl)-propionate in 1 ml of toluene were added a small amount of zinc-amalgam, 0.5 ml of conc. hydrochloric acid and 0.4 ml of water and the mixture was refluxed for 4 hours. After cooling, the mixture was filtered and the filtrate was extracted with benezene. The extract was washed with saturated sodium chloride solution and dried over anhydrous sodium sulfate. The solvent was distilled off to obtain yellow oil, which was subjected to thin-layer chromatography and there was obtained 26 mg of ethyl 2-(10,11-dihydro dibenzo[b,f]-thiepin-3-yl)-propionate as pale yellow oil.

NMR(CDCl$_3$)$\delta$: 1.16 (3H,t,J=7Hz,—CH$_2$C$\underline{H}_3$) 1.40 (3H,d,J=7Hz,=CHC$\underline{H}_3$) 3.20 (4H,s,—C$\underline{H}_2$C$\underline{H}_2$—) 3.50 (1H,q,J=7Hz,=C$\underline{H}$CH$_3$) 3.98 (2H,q,J=7Hz,—C$\underline{H}_2$CH$_3$) 6.80–7.36 (7H,m,aromatic protons).

EXAMPLE 12

2-(10,11-dihydro dibenzo[b,f]thiepin-3-yl)-propionic acid the mixture of 26 mg of ethyl 2-(10,11-dihydro dibenzo[b,f]thiepin-3-yl)-propionate, 1 ml of ethanol, 200 mg of potassium hydroxide and 1 ml of water was stirred at room temperature for 1 hour. The solvent was distilled off to obtain the residue, which was acidified with hydrochloric acid and the resulting mixture was extracted with ethyl acetate. The extract was washed with saturated sodium chloride solution and dried over anhydrous sodium sulfate. The solvent was distilled off to obtain 24 ml of 2-(10,11-dihydro dibenzo[b,f]thiepin-3-yl)-propionic acid as pale yellow oil.

IR($\nu_{max}$ $^{CHCl_3}$cm$^{-1}$): 1715 (C=O).

NMR(CDCl$_3$)$\delta$: 1.44 (3H,d,J—7Hz,=CHC$\underline{H}_3$); 3.26 (4H,s,—C$\underline{H}_2$C$\underline{H}_2$—); 3.60 (1H,q,J=7Hz,=C$\underline{H}$CH$_3$); 6.88–7.44 (7H,m,aromatic protons); 9.72 (1H,b.s,COO$\underline{H}$).

MS(m/e): 284 (M+).

EXAMPLE 13

2-(10,11-dihydro-11-oxo dibenzo[b,f]thiepin-3-yl)-propionic acid

The mixture of 83 mg of ethyl 2-(10,11-dihydro-11-oxo dibenzo[b,f]thiepin-3-yl)-propionate, 0.8 ml of ethanol, 120 mg of potassium hydroxide and 0.8 ml of water was stirred at room temperature for 2 hours. The solvent was distilled off to obtain the residue, which was acidified with hydrochloric acid and the resulting mixture was extracted with ethyl acetate. The extract was washed with saturated sodium chloride solution and dried over anhydrous sodium sulfate. The solvent was distilled off to obtain brown oil, which was chromatographed over silica gel, eluted with chloroform to give 59 mg of 2-(10,11-dihydro-11-oxo dibenzo[b,f]thiepin-3-yl)-propionic acid as pale yellow oil. The result in IR spectrum thereof is in accordance with that of the compound obtained in Example 9.

EXAMPLE 14

2-(10,11-dihydro-11-oxo dibenzo[b,f]oxepin-2-yl)-propionamide

To 730 mg of 2-[4'-(α-cyanoethyl)-phenoxy]-phenylacetic acid was added 15 g of polyphosphoric acid and the mixture was stirred at 100° C. for 0.5 hour. After cooling, to this were added pieces of ice and the mixture was extracted with ethyl acetate. The extract was washed with saturated sodium hydrogencarbonate solution, then saturated sodium chloride solution and dried over anhydrous sodium sulfate. The solvent was distilled off to obtain yellow oil, which was chromatographed over silica gel, eluted with chloroform, and there was obtained 378 mg of 2-(10,11-dihydro-11-oxo dibenzo[b,f]oxepin-2-yl)-propionamide as yellow oil. This was crystallized from ethyl acetate-n-hexane to give pale yellow crystals having a melting point of 154°–155° C.

IR($\nu_{max}^{KBr}$cm$^{-1}$): 3400, 3200 (NH$_2$), 1670 (C=O).

NMR(CDCl$_3$)δ: 1.42 (3H,d,J=7Hz,=CHC$\underline{H}_3$); 3.58 (1H,q,J=7Hz,=C$\underline{H}$CH$_3$); 4.02 (2H,s,COC$\underline{H}_2$); 6.08, 6.52 (2H,b.s,—CON$\underline{H}_2$); 6.84–7.62 (6H,m,aromatic protons); 7.92 (1H,d,J=3Hz,C$_1$—$\underline{H}$).

MS(m/e): 281 (m+).

EXAMPLE 15 ethyl 2-(10,11-dihydro-11-oxo dibenzo 8 b,f]oxepin-2-yl)-propionate

To 62 mg of 2-(10,11-dihydro-11-oxo dibenzo[b,f]oxepin-2-yl)-propionamide in 2 ml of ethanol were added three drops of conc. sulfuric acid and the mixture was reluxed with stirring for 4 hours. After the completion of the reaction, the solvent was distilled off to obtain the residue, to which was added ice and the resulting mixture was extracted with ethyl acetate. The extract was washed with saturated sodium hydrogencarbonate solution, then saturated sodium chloride solution and dried over anhydrous sodium sulfate. The solvent was distilled off to obtain brown oil, which was chromatographed over silica gel, eluted with chloroform and there was obtained 58 mg of ethyl 2-(10,11-dihydro-11-oxo dibenzo[b,f]oxepin-2-yl)-propionate as pale yellow oil.

IR($\nu_{max}^{KBr}$cm$^{-1}$): 1730, 1680 (C=O).

NMR(CDCl$_3$)δ: 1.10 (3H,t,J=7Hz,—CH$_2$C$\underline{H}_3$); 1.48 (3H,d,J=7Hz,=CHC$\underline{H}_3$); 3.72 (1H,q,J=7Hz,=C$\underline{H}$CH$_3$); 4.08 (2H,s,=C$\underline{H}_2$); 4.10 (2H,q,J=7Hz,—C$\underline{H}_2$CH$_3$); 7.10–7.64 (6H,m,aromatic protons); 7.97 (1H,d,J=3Hz,C$_1$13 $\underline{H}$).

MS(m/e): 310 (M+).

EXAMPLE 16

2-(10,11-dihydro-11-oxo dibenzo[b,f]oxepin-2-yl)-propionic acid

To 151 mg of ethyl2-(10,11-dihydro-11-oxo dibenzo[b,f]-oxepin-2-yl)-propionate in 2ml of ethanol was added 400 mg of potassium hydroxide in 2 ml of water and the mixture was stirred at room temperature for 0.5 hour. After the completion of the reaction, to this was added water and the mixture was extracted with benezene. The aqueous layer was acidified with hydrochloric acid and extracted with ethyl acetate. The extract was washed with saturated sodium chloride solution and dried over anhydrous sodium sulfate. The solvent was distilled off to obtain pale brown oil, which was chromatographed over silica gel, eluted with chloroform and there was obtained 112 mg of 2-(10,11-dihydro-11-oxo dibenzo[b,f]oxepin-2-yl)-propionic acid as pale yellow oil. This was crystallized from the mixed solvent of ethyl acetate-n-hexane to give pale yellow crystals having a melting point of 156°–157° C.

IR($\nu_{max}^{KBr}$cm$^{-1}$): 1700 (shoulder), 1680 (Ch=O).

NMR(CDCl$_3$)δ: 1.48 (3H,d,J=7Hz,=CHC$\underline{H}_3$); 3.72 (1H,q,J=7Hz,=C$\underline{H}$CH$_3$); 4.04 (2H,s,=C$\underline{H}_2$); 7.05–7.74 (6H,m,aromatic protons); 7.92 (1H,d,J=3Hz,C$_1$—$\underline{H}$).

MS(m/e): 282 (M+).

EXAMPLE 17

2-(10,11-dihydro dibenzo[b,f]oxepin-2-yl)-propionic acid

To 145 mg of 2-(10,11-dihydro-11-oxo dibenzo[b,f]oxepin-2-yl)-propionamide in 5 ml of ethanol were added 10 drops of hydrazine hydrate and the mixture was refluxed with stirring for 3 hours. After the completion of the reaction, the solvent was distilled off to obtain the residue, to which were added 10 ml of diethylene glycol and 500 mg of sodium hydroxide, and the resulting mixture was stirred at 132° to 133° C. for 1 hour. The reaction mixture was acidified with hydrochloric acid and extracted with ethyl acetate. The extract was re-extracted with saturated sodium hydrogencarbonate solution. This alkaline extract was acidified with hydrochloric acid and extracted with ethyl acetate. The extract was washed with saturated sodium chloride solution and dried over anhydrous sodium sulfate. The solvent was distilled off to obtain brown oil, which was chromatographed over silica gel, eluted with chloroform and there was obtained 65 mg of 2-(10,11-dihydro dibenxo[b,f]oxepin-2-yl)-propionic acid as pale yellow oil.

IR($\nu_{max}^{KBr}$cm$^{-1}$): 1710 (C=O)

NMR(CDCl$_3$)δ: 1.44 (3H,d,J=7Hz,=CHC$\underline{H}_3$); 3.10 (4H,s,—C$\underline{H}_2$C$\underline{H}_2$—); 3.63 (1H,q,J=7Hz,=C$\underline{H}$CH$_3$); 6.80–7.28 (7H,m,aromatic protons).

MS(m/e): 268 (M+).

EXAMPLE 18 ethyl 2-(10,11-dihydro dibenzo[b,f]oxepin-2-yl)-propionate

An amount of 190 mg of 2-(10,11-dihydro dibenzo[b,f]-oxepin-2-yl)-propionic acid was dissolved in 5 ml of ethanol containing 10% hydrogen chloride and the resulting mixture was stirred at room temperature for 1.5 hours. The solvent was distilled off to obtain the residue, which was extracted with ethyl acetate. The extract was washed with saturated sodium chloride solution and dried over anhydrous sodium sulfate. The solvent was distilled off to obtain pale brown oil, which was chromatographed over silica gel, eluted with benzene, and there was obtained 185 mg of ethyl 2-(10,11-dihydro dibenzo-[b,f]oxepin-2-yl)-propionate as pale yellow oil.

IR ($\nu_{max}^{KBr}$cm$^{-1}$): 1730 (C=O).

NMR(CDCl$_3$)δ: 1.18 (3H,t,J=7Hz,—CH$_2$C$\underline{H}_3$); 1.42 (3H,d,J=7Hz,=CHC$\underline{H}_3$); 3.12 (4H,s,—C$\underline{H}_2$C$\underline{H}_2$—); 3.62 (1H,q,J=7Hz,=C$\underline{H}$CH$_3$); 4.10 (2H,q,J=7Hz,—C$\underline{H}_2$CH$_3$); 6.86–7.28 (7H,m,aromatic protons).

MS(m/e): 296 (M+).

EXAMPLE 19

2-(10,11-dihydro dibenzo[b,f]oxepin-2-yl)-propionamide

To 132 mg of 2-(10,11-dihydro dibenzo[b,f]oxepin-2-yl)-propionic acid in 2 ml of benzene were added 0.6 ml of thionyl chloride and three drops of pyridine and the mixture was stirred at room temperature for 1 hour, then refluxed with stirring for 1 hour. The solvent was distilled off to obtain the residue, which was dissolved in 2 ml of chloroform and the resulting solution was added to 2 ml of 28% ammonia water. The mixture was stirred at room temperature for 3 hours. The reaction mixture was acidified with hydrochloric acid and extracted with ethyl acetate. The extract was washed with 1N-sodium hydroxide solution, then saturated sodium chloride solution and dried over anhydrous sodium sulfate. The solvent was distilled off to obtain yellowish brown oil, which was chromatographed over silica gel, eluted with chloroform/methanol (200/1). The eluate was crystallized from benzene-n-hexane to give 115 mg of 2-(10,11-dihydro dibenzo[b,f]oxepin-2-yl)-propionamide as pale yellow crystals having a melting point of 122.5°–123° C.

IR($\nu_{max}^{KBr}$cm$^{-1}$): 3320, 3160 (NH$_2$), 1660 (C=O);
NMR(CDCl$_3$)δ: 1.48 (3H,d,J=7Hz,=CHC$\underline{H}_3$); 3.12 (4H,s,—C$\underline{H}_2$C$\underline{H}_2$—); 3.52 (1H,q,J=7Hz,=C$\underline{H}$CH$_3$); 5.10, 5.90 (2H,b.s,—CON$\underline{H}_2$); 6.90–7.60 (7H,m,aromatic protons).
MS(m/e): 267 (M+).

EXAMPLE 20

2-(10,11-dihydro-11-oxo dibenzo[b,f]oxepin-3-yl)-propionamide

To 1.1 g of 2-[3'-(α-cyanoethyl)-phenoxyl]-phenylacetic acid was added 22 g of polyphosphoric acid and the mixture was stirred at 100° to 105° C. for 1 hours. After cooling, to this was added ice-water and the mixture was extracted with ethyl acetate. The extract was washed with saturated sodium carbonate solution, then saturated sodium chloride solution and dried over anyhdrous sodium sulfate. The solvent was distilled off to obtain brown oil, which was chromatographed over silica gel, eluted with n-hexane/acetone(5/1–1/1), and there was obtained 680 mg of 2-(10,11-dihydro-11-oxo dibenzo[b,f]oxepin-3-yl)-propionamide as pale brown oil. This was crystallized from chloroform and washed with n-hexane/acetone (2/1) to give colorless crystals having a melting point of 159°–160° C.

IR($\nu_{max}^{CHCl_3}$cm$^{-1}$): 3500, 3400 (CONH$_2$), 1680 (C=O).
NMR(CDCl$_3$)δ: 1.50 (3H,d,J=7Hz,=CHC$\underline{H}_3$); 3.67 (1H,q,J=7Hz,=C$\underline{H}$CH$_3$); 4.03 (2H,s,—CO—C$\underline{H}_2$—); 6.18, 6.48 (2H,b.s,—CON$\underline{H}_2$); 7.04–7.48 (6H,m,aromatic protons); 7.98 (1H,d,J=8Hz,C$_1$—$\underline{H}$).

EXAMPLE 21

2-(10,11-dihydro-11-oxo dibenzo[b,f]oxepin-3-yl)-propionic acid

The mixture of 340 mg of 2-(10,11-dihydro-11-oxo dibenzo[b,f]oxepin-3-yl)-propionamide, 3 ml of ethanol, 500 mg of potassium hydroxide and 3 ml of water was relfuxed for 8 hours. After cooling, ethanol was distilled off to obtain the residue, to which was added 1N-sodium hydroxide solution, and the mixture was extracted with ethyl acetate. The aqueous layer was acidified with hydrochloric acid and extracted with ethyl acetate. The extract was washed with saturated sodium chloride solution and dried over anhydrous sodium sulfate. The solvent was distilled off to obtain 380 mg of brown oil, which was chromatographed over silica gel to give 157 mg of 2-(10,11-dihydro-11-oxo dibenzo[b,f]oxepin-3-yl)-propionic acid as yellow oil.

IR($\nu_{max}^{CHCl_3}$cm$^{-1}$): 1715, 1680 (C=O).
NMR(CDCl$_3$)δ: 1.52 (3H,d,J=7Hz,=CHC$\underline{H}_3$); 3.76 (1H,q,J=7Hz,=C$\underline{H}$CH$_3$); 4.00 (2H,s,—CO—C$\underline{H}_2$—); 7.01–7.40 (6H,m,aromatic protons); 7.92 (1H,d,J=8Hz,C$_1$—$\underline{H}$); 10.36 (1H,b.s,COO$\underline{H}$).
MS (m/e): 282 (M+).

EXAMPLE 22 ethyl 2-(10,11-dihydro-11-oxo dibenzo[b,f]oxepin-3-yl)-propionate

To 50 mg of 2-(10,11-dihydro-11-oxo dibenzo[b,f]oxepin-3-yl)-propionamide in 2 ml of ethanol was added 0.2 ml of conc. sulfuric acid and the mixture was refluxed with stirring for 5 hours. The solvent was distilled off to obtain the residue, which was extracted with ethyl acetate. The extract was washed with saturated sodium chloride solution and dried over anhydrous sodium sulfate. The solvent was distilled off to obtain yellow oil, which was chromatographed over silica gel, eluted with chloroform and there was obtained 55 mg of ethyl 2-(10,11-dihydro-11-oxo dibenzo[b,f]oxepin-3-yl)-propionate as pale yellow oil.

IR($\nu_{max}^{KBr}$cm$^{-1}$): 1730, 1680 (C=O).
NMR(CDCl$_3$)δ: 1.10 (3H,t,J=7Hz,—CH$_2$C$\underline{H}_3$); 1.52 (3H,d,J=7Hz,=CHC$\underline{H}_3$); 3.74 (1H,q,J=7Hz,=C$\underline{H}$CH$_3$); 4.06 (2H,s,—COCH$_2$—); 4.11 (2H,q,J=7Hz,—C$\underline{H}_2$CH$_3$); 7.04–7.36 (6H,m,aromatic protons); 8.00 (1H,d,J=8Hz,C$_1$—$\underline{H}$).
MS(m/e): 310 (M+).

EXAMPLE 23 methyl 2-(10,11-dihydro-11-oxo dibenzo[b,f]oxepin-3-yl)-propionate.

To 100 mg of 2-(10,11-dihydro-11-oxo dibenzo[b,f]oxepin-3-yl)-propionamide in 2 ml of methanol was added 0.2 ml of conc. sulfuric acid and the mixture was refluxed with stirring for 4 hours. After cooling, the solvent was distilled off to obtain the residue, to which was added ice and the mixture was extracted with ethyl acetate. The extract was washed with saturated sodium chloride solution and dried over anhydrous sodium sulfate. The solvent was distilled off to obtain 95 mg of methyl 2-(10,11-dihydro-11-oxo dibenzo[b,f]oxepin-3-yl)-propionate as pale yellow oil.

IR($\nu_{max}^{CHCl_3}$cm$^{-1}$): 1730, 1680 (C=O)

EXAMPLE 24 methyl 2-(10,11-dihydro dibenzo[b,f]oxepin-3-yl)-propionate.

To 95 mg of methyl 2-(10,11-dihydro-11-oxo dibenzo[b,f]-oxepin-3-yl)-propionate in 1 ml of toluene were added a small amount of zinc-amalgam, 0.3 ml of conc. hydochloric acid and 0.2 ml of water, and the mixture was refluxed with stirring for 1 hour. After cooling, the mixture was filtered and the filtrate was extracted with benzene. The extract was washed with saturated sodium chloride solution and dried over anhydrous sodium sulfate. The solvent was distilled off to obtain pale yellow oil, which was subjected to thin-layer chromatography to give 30 mg of methyl 2-(10,11-dihydro dibenzo[b,f]oxepin-3-yl)-propionate as pale yellow oil.

NMR(CDCl$_3$)δ: 1.44 (3H,d,J=7Hz,=CHC$\underline{H}$$_3$); 3.14 (4H,s,—C$\underline{H}$$_2$C$\underline{H}$$_2$—); 3.56 (3H,s,—COOC$\underline{H}$$_3$); 3.60 (1H,q,J=7Hz,=C$\underline{H}$CH$_3$); 6.72–7.14 (7H,m,aromatic protons).

EXAMPLE 25

2-(10,11-dihydro dibenzo[b,f]oxepin-3-yl)-propionic acid.

The mixture of 30 mg of methyl 2-(10,11-dihyoro dibenzo[b,f]oxepin-3-yl)-propionate, 1 ml of ethanol, 200 mg of potassium hydroxide and 1 ml of water was stirred at room temperature for 15 minutes. The solvent was distilled off to obtain the residue, which was acidified with hydrochloric acid and the resulting mixture was extracted with ethyl acetate. The extract was washed with saturated sodium chloride solution and dried over anhydrous sodium sulfate. The solvent was distilled off to obtain 28.4 mg of 2-(10,11-dihydro dibenzo[b,f]oxepin-3-yl)-propionic acid as pale yellow oil.

IR($\nu_{max}^{KBr}$cm$^{-1}$): 1705 (C=O).

NMR(CDCl$_3$)δ: 1.42 (3H,d,J=7Hz,=CHC$\underline{H}$$_3$); 2.99 (4H,s,—C$\underline{H}$$_2$C$\underline{H}$$_2$—); 3.56 (1H,q,J=7Hz,=C$\underline{H}$CH$_3$); 6.70–7.14 (7H,m,aromatic protons).

MS(m/e): 268 (M+).

EXAMPLE 26

2-(10,11-dihydro-11-oxo dibenzo[b,f]oxepin-4-yl)-propionamide.

To 349 mg of 2-[2'-(α-cyanoethyl)-phenoxy]-phenylacetic acid was added 7 g of polyphosphoric acid and the mixture was stirred at 87°–89° C. for 2 hours. To this were added pieces of ice and the mixture was extracted with ethyl acetate and the extract was washed with saturated sodium hydrogencarbonate solution, then saturated sodium chloride solution and dried over anhydrous sodium sulfate. The solvent was distilled off to obtain yellow oil, which was chromatographed over silica gel, eluted with chloroform and crystallized from acetone-n-hexane to give 292 mg of 2-(10,11-dihydro-11-oxo dibenzo[b,f]oxepin-4-yl)-propionamide as pale yellow crystals having a melting point of 177°–178.5° C.

IR($\nu_{max}^{KBr}$cm$^{-1}$): 3430 (NH$_2$), 1670 (C=O).

MS(m/e): 281 (M+).

EXAMPLE 27

2-(10,11-dihydro-11-oxo dibenzo[b,f]oxepin-4-yl)-propionic acid.

To 100 mg of 2-(10,11-dihydro-11-oxo dibenzo[b,f]oxepin-4-yl)-propionamide in 2 ml of ethanol was added 400 mg of potassium hydroxide in 2 ml of water and the mixture was refluxed with stirring for 6.5 hours. After the completion of the reaction, the solvent was distilled off to obtain the residue, to which was added 2N-sodium hydroxide solution, and the resulting mixture was extracted with ethyl acetate. The aqueous layer was acidified with hydrochloric acid and extracted with ethyl acetate. The extract was washed with saturated sodium chloride solution and dried over anhydrous sodium sulfate. The solvent was distilled off to obtain brown oil, which was chromatographed over silica gel, eluted with chloroform and crystallized from acetone-n-hexane to give 85 mg of 2-(10,11-dihydro-11-oxo dibenzo[b,f]oxepin-4-yl)-propionic acid as pale yellow crystals having a melting point of 159°–160° C.

IR($\nu_{max}^{KBr}$cm$^{-1}$): 1710, 1680 (C=O).

NMR[(CD$_3$)$_2$CO]δ: 1.59 (3H,d,J=7Hz,=CHC$\underline{H}$$_3$); 4.10 (2H,s,—C$\underline{H}$$_2$CO—); 4.54 (1H,q,J=7Hz,=C$\underline{H}$CH$_3$); 7.12–8.02 (7H,m,aromatic protons).

MS(m/e): 282 (M+).

EXAMPLE 28

2-(10,11-dihydro dibenzo[b,f]oxepin-4-yl)-propionic acid.

To 80 mg of 2-(10,11-dihydro-11-oxo dibenzo[b,f]oxepin-4-yl)-propionamide in 4 ml of ethanol was added 0.3 ml of hydrazine hydrate and the mixture was refluxed with stirring for 8 hours. The solvent was distilled off to obtain pale yellow oil, to which were added 3 ml of diethylene glycol and 400 mg of sodium hydroxide, and the resulting mixture was stirred at 125° C. for 1 hour. To the mixture was added water and the resulting solution was acidified with hydrochloric acid and extracted with ethyl acetate. The organic layer was extracted with saturated sodium hydrogencarbonate solution. The aqueous layer was acidified with hydrochloric acid and extracted with ethyl acetate. The extract was washed with saturated sodium chloride solution and dried over anhydrous sodium sulfate. The solvent was distilled off to obtain pale yellow crystals, which were recrystallized from benzene-n-hexane, and there was obtained 37 mg of 2-(10,11-dihydro dibenzo[b,f]oxepin-4-yl)-propionic acid as pale yellow crystals having a melting point of 133°–133.5° C.

IR($\nu_{max}^{KBr}$cm$^{-1}$): 1700 (C=O).

NMR(CDCl$_3$)δ: 1.50 (3H,d,J=7Hz,=CHC$\underline{H}$$_3$); 3.10 (4H,s,—C$\underline{H}$$_2$C$\underline{H}$$_2$—); 4.30 (1H,q,J=7Hz,=C$\underline{H}$CH$_3$); 6.80–7.30 (7H,m,aromatic protons); 9.48 (1H,b.s,—COO$\underline{H}$).

MS(m/e): 268 (M+).

EXAMPLE 29

2-(5,6-dihydro-6-oxo benzo[b]pyrido[3,2-f]thiepin-8-yl)-propionamide.

The mixture of 101 mg of 2-[4'-(α-cyanoethyl)-phenylthio]-3-pyridylacetic acid and 2 g of polyphosphoric acid was stirred at 150° C. for 65 minutes. After cooling, to this was added ice-water and the mixture was neutralized with conc. sodium hydroxide solution and 3% sodium hydroxide solution, then was made alkaline therewith. The resulting mixture was extracted with ethyl acetate and the extract was washed with 3% sodium hydroxide solution and dried over anhydrous sodium sulfate. The solvent was distilled off to obtain 36 mg of yellow glutinous substance, which was chromatographed over silica gel, eluted with n-hexane/acetone (2/1) and there was obtained 25 mg of 2-(5,6-dihydro-6-oxo benzo[b]pyrido[3,2-f]-thiepin-8-yl)-propionamide as colorless glutinous substance. This was solidified with ethanol to give crystals having a melting point of 175°–180° C. These were recrystallized from ethanol to give crystals having a melting point of 190°–192.5° C.

IR($\nu_{max}^{CHCl_3}$cm$^{-1}$): 3520, 3420 (NH$_2$), 1680 (C=O).

NMR[(CD$_3$)$_2$SO]δ: 1.23 (3H,d,J=8Hz,=CHC$\underline{H}$$_3$); 3.12 (2H,s,—CON$\underline{H}$$_2$); 3.54 (1H,q,J=8Hz,=C$\underline{H}$CH$_3$); 4.16 (2H,s,—COC$\underline{H}$$_2$—); 6.40–8.40 (6H,m,aromatic protons).

EXAMPLE 30

2-(5,6-dihydro-6-oxo benzo[b]pyrido[3,2-f]thiepin-8-yl)-propionic acid.

To 101 mg of 2-(5,6-dihydro-6-oxo benzo[b]pyrido[3,2-f]-thiepin-8-yl)-propionamide were added 0.4 g of potassium hydroxide, 1 ml of water and 4 ml of ethanol and the mixture was refluxed with stirring for 5 hours. After cooling, to this were added water and 3% sodium hydroxide solution, then a small amount of diethyl ether, and the mixture was shaked. The aqueous layer was collected and acidified with acetic acid, and to this was added sodium chloride, and the resulting mixture was extracted with chloroform. The extract was washed with saturated sodium chloride solution and dried over anhydrous sodium sulfate. The solvent was distilled off to obtain 115 mg of brown glutinous substance, which was chromatographed over silica gel, eluted with chloroform/methanol(100/1-20/1), and there was obtained 83 mg of 2-(5,6-dihydro-6-oxo benzo[b]pyrido[3,2-f]thiepin-8-yl)-propionic acid as colorless glutinous substance. This was solidified by washing with n-hexane and there was obtained colorless crystals having a melting point of 141°–143° C.

IR($\nu_{max}^{KBr}$cm$^{-1}$): 1720, 1670 (C=O).

NMR(CDCl$_3$)$\delta$: 1.46 (3H,d,J=8Hz,=CHC$\underline{H}_3$); 3.70 (1H,q,J=8Hz,=C$\underline{H}$CH$_3$); 4.24 (2H,s,—COC$\underline{H}_2$—); 7.00–8.40 (6H,m,aromatic protons).

MS (m/e): 299 (M+)

EXAMPLE 31 methyl 2-(5,6-dihydro-6-oxo benzo[b]pyrido[3,2-thiepin-8-yl)-propionate.

To 54 mg of 2-(5,6-dihydro-6-oxo benzo[b]pyrido[3,2-f]-thiepin-8-yl)-propionic acid in ethanol was added 5 ml of diazomethane etherial solution and the mixture was stirred at room temperature for 1 hour. To this was added acetic acid to decompose an excess reagent, then saturated sodium hydrogen-carbonate solution to make the solution alkaline, and the mixture was extracted with ethyl acetate. The extract was washed with saturated sodium chloride solution and dried over anhydrous sodium sulfate. The solvent was distilled off to obtain 51 mg of oily substance, which was chromatographed over silica gel, eluted with benzene/chloroform (1/1) to obtain the colorless oily substance, which was crystallized from ethanol to give 40 mg of methyl 2-(5,6-dihydro-6-oxo benzo[b]pyrido[3,2-f]thiepin-8-yl)-propionate as colorless crystals having a melting point of 98°–99.5° C.

IR($\nu_{max}^{CHCl_3}$cm$^{-1}$): 1730, 1680 (C=O).

NMR(CDCl$_3$)$\delta$: 1.45 (3H,d,J=8Hz,=CHC$\underline{H}_3$); 3.60 (3H,s,—COOC$\underline{H}_3$ and 1H,m,=C$\underline{H}$CH$_3$); 4.22 (2H,s,—COC$\underline{H}_2$—); 7.20–8.02 (6H,m,aromatic protons).

MS(m/e): 313 (M+).

EXAMPLE 32

2-(5,6-dihydro-6-hydrazo benzo[b]pyrido[3,2-f]thiepin-8-yl)-propionamide.

The mixture of 134 mg of 2-(5,6-dihydro-6-oxo benzo[b]-pyrido[3,2-f]thiepin-8-yl)-propionamide, 1.5 ml of hydrazine hydrate and 10 ml of ethanol was refluxed with stirring for 1.5 hours. The solvent was distilled off to obtain the residue, which was dissolved in chloroform, and the resulting mixture was washed with water and dried over anhydrous sodium sulfate. The solvent was distilled off to obtain 139 mg of 2-(5,6-dihydro-6-hydrazo benzo[b]pyrido[3,2-f]thiepin-8-yl)-propionamide as pale yellow crystals.

IR($\nu_{max}^{KBr}$cm$^{-1}$): 3600–3300 (NH$_2$), 1660 (C=O).

MS(m/e): 312 (M+).

EXAMPLE 33

2-(5,6-dihydro benzo[b]pyrido[3,2-f]thiepin-8-yl)-propionic acid.

The mixture of 74 mg of 2-(5,6-dihydro-6-hydrazo benzo[b]-pyrido[3,2-f]thiepin-8-yl)-propionamide, 1.8 g of potassium hydroxide and 18 ml of diethylene glycol was stirred at 130° to 140° C. for 4 hours. After cooling, to this was added water and the mixture was acidified with acetic acid and extracted with chloroform. After washing with water, the mixture was dried over anhydrous sodium sulfate. The solvent was distilled off to obtain brown oil, which was chromatographed over silica gel, eluted with chloroform-methanol, and there was obtained 36 mg of 2-(5,6-dihydro benzo[b]pyrido[3,2-f]thiepin-8-yl)-propionic acid as pale yellow oil. This was crystallized from ethyl acetate to give colorless crystals having a melting point of 181°–183° C.

IR($\nu_{max}^{KBr}$cm$^{-1}$): 1700 (C=O)

NMR[(CD$_3$)$_2$SO]$\delta$: 1.30 (3H,d,J=8Hz,=CHC$\underline{H}_3$); 3.12 (4H,m,—C$\underline{H}_2$C$\underline{H}_2$—); 3.58 (1H,q,J=8Hz,=C$\underline{H}$CH$_3$); 7.00–8.40 (6H,m,aromatic protons).

EXAMPLE 34 ethyl 2-(5,6-dihydro benzo[b]pyrido[3,2-f]thiepin-8-yl)-propionate.

An amount of 30 mg of 2-(5,6-dihydro benzo[b]pyrido[3,2-f]-thiepin-8-yl)-propionic acid was dissolved in 2 ml of ethanol saturated with hydrogen chloride and the mixture was stirred at room temperature for 1 hour. After the completion of the reaction, the mixture was made alkaline with saturated sodium hydrogencarbonate solution and extracted with chloroform, and the extract was washed with water, then saturated sodium chloride solution and dried over anhydrous sodium sulfate. The solvent was distilled off to obtain yellow oil, which was chromatographed over silica gel, eluted with benzene-chloroform, and there was obtained 27 mg of ethyl 2-(5,6-dihydro benzo[b]pyrido[3,2-f]-8-yl)-propionate as colorless oil.

IR($\nu_{max}^{CHCl_3}$cm$^{-1}$): 1725 (C=O).

NMR (CDCl$_3$)$\delta$: 1.20 (3H,t,J=7Hz, 13 CH$_2$C$\underline{H}_3$); 1.42 (3H,d,J=7Hz,=CHC$\underline{H}_3$); 3.20 (4H,m,—C$\underline{H}_2$C$\underline{H}_2$—) ; 3.58 (1H,m,=C$\underline{H}$CH$_3$); 4.10 (2H,m,—C$\underline{H}_2$CH$_3$); 7.00–8.30 (6H,m,aromatic protons).

MS(m/e): 313 (M+).

EXAMPLE 35

2-(5,6-dihydro benzo[b]pyrido[3,2-f]thiepin-8-yl)-propionamide.

An amount of 50 mg of 2-(5,6-dihydro benzo[b]pyrido[3,2-f]-thiepin-8-yl)-propionic acid was dissolved in the mixed solvents of 20 ml of methylene chloride and 20 drops of chloroform by heating, and to this were added 50 mg of dicyclohexylcarbodiimide with ice-cooling, then dropwise 3 ml of methylene chloride saturated with liquid ammonia. The resulting mixture was stirred for 1.5 hours under a stream of nitrogen. After the completion of the reaction, to the mixture were added pieces of ice and acetic acid and the resulting mixture was extracted with chloroform. The extract was washed with saturated sodium hydrogencarbonate solution, then saturated sodium chloride solution and dried over anhydrous sodium sulfate. The solvent was distilled off to obtain the residue, which was chromatographed over silica gel, eluted with n-hexane/acetone (4/1–1/1), and there was obtained colorless solid. This was recrystallized from ethyl acetate to give 38 mg of 2-(5,6-dihydro benzo[b]pyrido[3,2-f]-thiepin-8-yl)-propionamide as colorless crystals having a melting point of 173.5°–175° C.

IR($\nu_{max}^{KBr}$cm$^{-1}$): 3350, 3160 (NH$_2$), 1680 (C=O).
NMR(CDCl$_3$)δ: 1.44 (3H,d,J=7Hz,=CHC$\underline{H}_3$) 3.04–3.25 (4H,m,—C$\underline{H}_2$CH$_2$—) 3.45 (1H,q,J=7Hz,=C$\underline{H}$CH$_3$) 5.50 (2H,b.s.,—CON$\underline{H}_2$) 6.80–8.10 (6H,m,aromatic protons).
MS (m/e): 284 (M$^+$).

EXAMPLE 36

2-(5,6-dihydro-6-oxo benzo[b]pyrido[3,2-f]thiepin-9-yl)-propionamide

The mixture of 6 g of 2-[3'-(α-cyanoethyl)-phenylthio]-3-pyridylacetic acid and 120 g of polyphosphoric acid was stirred at 160° C. for 2 hours. After cooling, to this was added ice-water and the resulting mixture was alkalified with conc. ammonia and extracted with chloroform. The extract was washed with saturated sodium chloride solution and dried over anhydrous sodium sulfate. The solvent was distilled off to obtain the glutinous substance, which was chromatographed over silica gel, eluted with chloroform/ethanol(50/1) and there was obtained solid substance. This was recrystallized from chloroform-n-hexane to give 1.8 g of 2-(5,6-dihydro-6-oxo benzo[b]pyrido[3,2-f]thiepin-9-yl)-propionamide as pale yellow powder having a melting point of 161°–162° C.

IR($\nu_{max}^{CHCl_3}$cm$^{-1}$): 3540, 3420 (NH$_2$), 1680 (C=O).
NMR[(CD$_3$)$_2$SO]δ: 1.30 (3H,d,J=7Hz,=CHC$\underline{H}_3$) 3.22 (2H,s,—CON$\underline{H}_2$), 3.61 (1H,q,J=7Hz,=C$\underline{H}$CH$_3$), 4.24 (2H,s,—COC$\underline{H}_2$—), 6.70–8.36 (6H,m,aromatic protons).
MS(m/e): 298 (M$^+$).

EXAMPLE 37

2-(5,6-dihydro-6-oxo benzo[b]pyrido[3,2-f]thiepin-9-yl)-propionic acid

The mixture of 100 mg of 2-(5,6-dihydro-6-oxo benzo[b]-pyrido[3,2-f]thiepin-9-yl)-propionamide, 170 mg of potassium hydroxide, 1.5 ml of water and 3 ml of ethanol was refluxed for 5 hours. After cooling, the solvent was distilled off to obtain the residue, to which was added ice-water and the resulting mixture was acidified with acetic acid and extracted with chloroform. The extract was washed with water and dried over anhydrous sodium sulfate. The solvent was distilled off to obtain the solid substance, which was recrystallized from benzene to give 70 mg of 2-(5,6-dihydro-6-oxo benzo[b]pyrido-[3,2-f]thiepin-9-yl)-propionic acid as pale yellow powder having a melting point of 150°–151° C.

IR($\nu_{max}^{KBr}$cm$^{-1}$): 1720, 1680 (C=O)
NMR[(CD$_3$)$_2$SO]δ: 1.36 (3H,d,J=7Hz,=CHC$\underline{H}_3$); 3.73 (1H,q,J=7Hz,=C$\underline{H}$CH$_3$); 4.22 (2H,s,—COC$\underline{H}_2$—); 7.12–8.04 (5H,m,aromatic protons); 8.32 (1H,d,J=5Hz,aromatic proton).
MS(m/e): 299 (M$^+$)

EXAMPLE 38 methyl 2-(5,6-dihydro-6-oxo benzo[b]pyrido[3,2-f]thiepin-9-yl)-propionate

To 30 mg of 2-(5,6-dihydro-6oxo benzo[b]pyrido[3,2-f]-thiepin-9-yl)-propionic acid in 5 ml of ethanol was added dropwise etherial solution of diazomethane at 0° C. After 2 minutes, to this was added acetic acid to decompose an excess of the reagent, then were added chloroform and water. The organic layer was collected, washed with 5% sodium hydrogencarbonate solution, then saturated sodium chloride solution, and dried over anhydrous sodium sulfate. The solvent was distilled off to obtain the residue, which was chromatographed over silica gel, eluted with benzene/chloroform(4/1) and there was obtained 30 mg of methyl 2-(5,6-dihydro-6-oxo benzo[b]pyrido[3,2-f]thiepin-9-yl)-propionate as colorless glutinous substance.

IR($\nu_{max}^{CCl_4}$cm$^{-1}$): 1740, 1680 (C=O);
NMR(CDCl$_3$)δ: 1.50 (3H,d,J=7Hz,=CHC$\underline{H}_3$); 3.70 (3H,s,—COOC$\underline{H}_3$); 3.76 (1H,q,J=7Hz,=C$\underline{H}$CH$_3$); 4.31 (2H,s,—COC$\underline{H}_2$—); 7.20–8.24 (5H,m,aromatic protons); 8.40 (1H,d,J=4Hz,aromatic proton).
MS(m/e): 313 (M$^+$).

EXAMPLE 39

2-(5,6-dihydro-6-hydrazo benzo[b]pyrido[3,2-f]thiepin-9-yl)-propionamide

The mixture of 400 mg of 2-(5,6-dihydro-6-oxo benzo[b]-pyrido[3,2-f]thiepin-9-yl)-propionamide, 1 g of hydrazine hydrate and 10 ml of ethanol was refluxed for 3 hours. After cooling, the mixture was freed of solvent to dryness by evaporation to obtain the residue, which was recrystallized from benzene/ethanol (10/1) to give 350 mg of 2-(5,6-dihydro-6-hydrazo benzo[b]-pyrido[3,2-f]thiepin-9-yl)-propionamide as pale yellow powder.

IR($\nu_{max}^{KBr}$cm$^{-1}$): 3400–3170 (NH$_2$), 1670 (C=O).
MS(m/e): 312 (M$^+$).

EXAMPLE 40

2-(5,6-dihydro benzo[b]pyrido[3,2-f]thiepin-9-yl)-propionic acid

The mixture of 300 mg of 2-(5,6-dihydro-6-hydrazo benzo-[b]pyrido[3,2-f]thiepin-9-yl)-propionamide, 15 ml of diethylene glycol and 1.5 g of potassium hydroxide was stirred at 130° C. for 2 hours. After cooling, the mixture was acidified with acetic acid and extracted with chloroform, and the extract was washed with saturated sodium chloride solution and dried over anhydrous sodium sulfate. The solvent was distilled off to obtain the residue, which was chromatographed over silica gel, eluted with chloroform and there was obtained the solid substance. This was recrystallized from benzene to give 150 mg of 2-(5,6-dihydro benzo[b-]pyrido[3,2-f]thiepin-9-yl)-propionic acid as colorless crystals having a melting point of 161°–162° C.

IR($\nu_{max}^{KBr}$cm$^{-1}$): 1720 (C=O).
NMR[(CD$_3$)$_2$SO]δ: 1.30 (3H,d,J=7Hz,=CHC$\underline{H}_3$), 2.90–3.32 (4H,broad doublet,—C$\underline{H}_2$C$\underline{H}_2$—), 3.56 (1H,q,J=7Hz,=C$\underline{H}$CH$_3$), 6.96–7.52 (5H,m,aromatic protons), 8.14 (1H,d,J=5Hz,aromatic proton).
MS(m/e): 285 (M$^+$).

EXAMPLE 41 ethyl 2-(5,6-dihydro benzo[b]pyrido[3,2-f]thiepin-9-yl)-propionate

To 40 mg of 2-(5,6-dihydro benzo[b]pyrido[3,2-f]thiepin-9-yl)-propionic acid was added 15 ml of ethanol containing hydrogen chloride and the mixture was stirred at room temperature for 3 hours. The solvent was distilled off to obtain the residue, to which was added ice-water, and the resulting mixture was alkalified with 5% sodium hydrogencarbonate and extracted with ethyl acetate. The extract was washed with water and dried over anhydrous sodium sulfate. The solvent was distilled off to obtain oily substance, which was chromatographed over silica gel, eluted with benzene/chloroform(1/1), and there was obtained 35 mg of ethyl 2-(5,6-dihydro benzo[b]pyrido[3,2-f]thiepin-9-yl)-propionate as oil.

IR($\nu_{max}^{CCl_4}$cm$^{-1}$): 1735 (C=O).
NMR(CCl$_4$)$\delta$: 1.17 (3H,t,J=7Hz,—CH$_2$C$\underline{H}_3$), 1.40 (3H,d,J=7Hz,=CHC$\underline{H}_3$), 2.94-3.28 (4H,m,—C$\underline{H}_2$CH$_2$—), 3.51 (1H,q,J=7Hz,=C$\underline{H}$CH$_3$), 4.00 (2H,q,J=7Hz,—C$\underline{H}_2$CH$_3$), 6.70-7.36 (5H,m,aromatic protons), 8.07 (1H,d,J=4Hz,C$_2$—$\underline{H}$).
MS(m/e): 313 (M+).

EXAMPLE 42

2-(5,6-dihydro benzo[b]pyrido[3,2-f]thiepin-9-yl)-propionamide

The mixture of 80 mg of 2-(5,6-dihydro benzo[b]pyrido-[3,2-f]thiepin-9-yl)-propionic acid, 120 mg of dicyclohexylcarbodiimide and 5 ml of chloroform was stirred at 0° C. for 20 minutes under a stream of nitrogen. To this was added dropwise 1 ml of chloroform containing excessive amount of ammonia and the resulting mixture was stirred for 2 hours at 0° C., then at room temperature for 1 hour. To this was added 50 g of ice-water and the mixture was acidified with acetic acid and extracted with chloroform. The extract was washed with water, 5% sodium hydrogencarbonate solution, then water, and dried over anhydrous sodium sulfate. The solvent was distilled off to obtain the residue, which was dissolved in ethyl acetate and filtered. The filtrate was freed of the solvent to obtain the residue, which was chromatographed over silica gel, eluted with chloroform/ethanol(100/1), and there was obtained 63 mg of 2-(5,6-dihydro benzo[b]pyrido[3,2-f]thiepin-9-yl)-propionamide as colorless glutinous substance.

IR($\nu_{max}^{CHCl_3}$cm$^{-1}$): 3530, 3400, (NH$_2$), 1680 (C=O), NMR(CDCl$_3$)$\delta$: 1.44 (3H,d,J=7Hz,=CHC$\underline{H}_3$), 3.00-3.30 (4H,m,—C$\underline{H}_2$CH$_2$—), 3.48 (1H,q,J=7Hz,=C$\underline{H}$CH$_3$), 5.60-6.08 (2H,broad s,—CON$\underline{H}_2$), 6.80-7.40 (5H,m,aromatic protons), 8.16 (1H,d,J=4Hz,aromatic proton).
MS(m/e): 284 (M+).

EXAMPLE 43

2-(5,6-dihydro-6-oxo benzo[b]pyrido[3,2-f]oxepin-8-yl)-propionamide

To 147 mg of 2-[4'-(α-cyanoethyl)phenoxy]-3-pyridylacetic acid was added 3 g of polyphosphoric acid and the mixture was stirred at 130° C. for 3 hours. After cooling, to this was added ice-water and the resulting mixture was alkalified with sodium hydroxide and extracted with ethyl acetate. The extract was washed with water and dried over anhydrous sodium sulfate. The solvent was distilled off to obtain 32 mg of brown solid, which was chromatographed over silica gel, eluted with chloroform and subjected to the thin-layer chromatography, and there was obtained 15 mg of 2-(5,6-dihydro-6-oxo benzo[b]pyrido-[3,2-f]oxepin-8-yl)-propionamide as colorless crystals having a melting point (decomposition) of 200°-220° C.

IR($\nu_{max}^{KBr}$cm$^{-1}$): 3440, 3180 (NH$_2$), 1680 (C=O).
NMR[(CD$_3$)$_2$SO]$\delta$: 1.30 (3H,d,J=7Hz,=CHC$\underline{H}_3$), 3.66 (1H,q,J=7Hz,=C$\underline{H}$CH$_3$), 4.10 (2H,s,—COC$\underline{H}_2$—), 6.80 (1H,s—CON$\underline{H}_2$), 7.30-8.40 (7H,m,aromatic protons and —CON$\underline{H}_2$).
MS(m/e): 282 (M+).

EXAMPLE 44

2-(5,6-dihydro-6-oxo benzo[b]pyrido[3,2-f]oxepin-8-yl)-propionic acid

The mixture of 100 mg of 2-(5,6-dihydro-6-oxo benzo[b]-pyrido[3,2-f]oxepin-8-yl)-propionamide, 400 mg of potassium hydroxide, 1.25 ml of water and 3.75 ml of ethanol was refluxed with stirring for 6 hours. After cooling, to this was added water and the resulting mixture was washed with ethyl acetate. The aqueous layer was acidified with acetic acid and extracted with ethyl acetate. The extract was washed with saturated sodium chloride solution and dried over anhydrous sodium sulfate. The solvent was distilled off to obtain 106 mg of the residue, which was chromatographed over silica gel, eluted with cloroform, and there was obtained 52 mg of 2-(5,6-dihydro-6-oxo benzo[b]-pyrido[3,2-f]oxepin-8-yl)-propionic acid as pale yellow oil.

IR($\nu_{max}^{CHCl_3}$cm$^{-1}$): 1710, 1685 (C=O).
NMR(CDCl$_3$)$\delta$: 1.50 (3H,d,J=8Hz,=CHC$\underline{H}_3$), 3.74 (1H,q,J=8Hz,=C$\underline{H}$CH$_3$), 4.03 (2H,s,—COC$\underline{H}_2$—), 7.20-8.30 (6H,m,aromatic protons).
MS(m/e): 283 (M+).

EXAMPLE 45

2-(5,6-dihydro benzo[b]pyrido[3,2-f]oxepin-8-yl)-propionic acid

To 300 mg of 2-(5,6-dihydro-6-oxo benzo[b]-pyrido[3,2-f]-oxepin-8-yl)-propionamide in 30 ml of ethanol was added dropwise 5 ml of hydrazine hydrate and the mixture was refluxed with stirring for 1 hour. After the completion of the reaction, the solvent was distilled off to obtain the solid substance, to which were added 30 ml of diethylene glycol and 700 mg of sodium hydroxide, and the resulting mixture was stirred at 130° C. for 3 hours under a stream of nitrogen. After cooling, to this was added water and the mixture was washed with ethyl acetate. The aqueous layer was acidified with acetic acid and extracted with ethyl acetate, and the extract was washed with saturated sodium chloride solution and dried over anhydrous sodium sulfate. The solvent was distilled off to obtain the residue, which was chromatographed over silica gel, eluted with n-hexane/acetone (5/1-2/1), and there was obtained 29 mg of oil. This was crystallized from ethyl acetate to give 17 mg of 2-(5,6-dihydro benzo[b]pyrido[3,2-f]-oxepin-8-yl)-propionic acid as colorless needles having a melting point of 182.5°-184° C.

IR($\nu_{max}^{KBr}$cm$^{-1}$): 1710 (C=O).
NMR(CDCl$_3$)$\delta$: 1.50 (3H,d,J=8Hz,=CHC$\underline{H}_3$), 3.04 (4H,s,—C$\underline{H}_2$C$\underline{H}_2$—), 3.65 (1H,q,J=8Hz,=C$\underline{H}$CH$_3$), 6.90-8.10 (6H,m,aromatic protons).
MS(m/e): 269 (M+).

EXAMPLE 46 ethyl 2-(5,6-dihydro benzo[b]pyrido[3,2-f]oxepin-8-yl)-propionate

The mixture of 30 mg of 2-(5,6-dihydro benzo[b-]pyrido[3,2-f]-oxepin-8-yl)-propionic acid in 0.5 ml of ethanol and 2 ml of ethanol saturated with hydrogen chloride gas was stirred at room temperature for 1 hour. The mixture was alkalified with saturated sodium hydrogencarbonate and extracted with chloroform. The extract was washed with saturated sodium chloride solution and dried over anhydrous sodium sulfate. The solvent was distilled off to obtain oily substance, which was chromatographed over silica gel, eluted with chloroform/benzene(1/4–1/3), and there was obtained 30 mg of ethyl 2-(5,6-dihydro benzo[b]pyrido-[3,2-f]oxepin-8-yl)-propionate as colorless oil.

IR($\nu_{max}^{CCl_4}$cm$^{-1}$): 1730 (C=O).

NMR(CCl$_4$)δ: 1.10 (3H,t,J=8Hz,—CH$_2$C$\underline{H}_3$), 1.35 (3H,d,J=7Hz,=CHC$\underline{H}_3$), 2.94 (4H,s,—C$\underline{H}_2$C$\underline{H}_2$—), 3.33 (1H,q,J=7Hz,=C$\underline{H}$CH$_3$), 3.84 (2H,q,J=8Hz,—C$\underline{H}_2$CH$_3$), 6.50-7.78 (6H,m,aromatic protons).

MS(m/e): 297 (M+).

EXAMPLE 47

2-(5,6-dihydro benzo[b]pyrido[3,2-f]oxepin-8-yl)-propionamide

To 10 ml of methylene chloride solution containing 50 mg of 2-(5,6-dihydro benzo[b]pyrido[3,2-f]oxepin-8-yl)-propionic acid and 50 mg of dicyclohexylcarbodiimide was added 5 ml of methylene chloride saturated with ammonia, and the mixture was stirred with ice-cooling for 2 hours. To this were added acetic acid and ice and the resulting mixture was extracted with chloroform. The extract was washed with saturated sodium hydrogencarbonate solution, then saturated sodium chloride solution, and dried over anhydrous sodium sulfate. The solvent was distilled off to obtain the residue, which was extracted with ethyl acetate and the extract was freed of the solvent. The resulting residue was chromatographed over silica gel, eluted with n-hexane/acetone (4/1–1/1), and there was obtained 22 mg of 2-(5,6-dihydro benzo[b]pyrido[3,2-f]oxepin-8-yl)-propionamide as white crystals. These were recrystallized from ethyl acetate to give colorless crystals having a melting point of 162°-165° C.

IR($\nu_{max}^{KBr}$cm$^{-1}$): 3350, 3180 (NH$_2$), 1680 (C=O).

NMR(CDCl$_3$)δ: 1.50 (3H,d,J=7Hz,=CHC$\underline{H}_3$) 3.11 (4H,s,—C$\underline{H}_2$C$\underline{H}_2$—) 3.55 (1H,q,J=7Hz,=C$\underline{H}$CH$_3$) 5.75 (2H,broad s,—N$\underline{H}_2$) 6.95-8.15 (6H,m,aromatic protons).

MS(m/e): 268 (M+).

EXAMPLE 48

2-(5,6-dihydro-6-oxo benzo[b]pyrido[3,2-f]oxepin-9-yl)-propionamide

The mixture of 1.3 g of 2-[3'-(α-cyanoethyl)-phenoxy]-3-pyridylacetic acid and 30 g of polyphosphoric acid was stirred at 150° C. for 2 hours. After cooling, to this was added ice-water and the mixture was alkalified with 10% ammonia water and extracted with chloroform. The extract was washed with saturated sodium chloride solution and dried over anhydrous sodium sulfate. The solvent was distilled off to obtain the oil, which was chromatographed over silica gel, eluted with chloroform/ethanol (50/1), and there was obtained a solid substance. This was recrystallized from methanol to give 250 mg of 2-(5,6-dihydro-6-oxo benzo[b-]pyrido[3,2-f]oxepin-9-yl)-propionamide as pale yellow powder having a melting point of 89°-90° C.

IR($\nu_{max}^{CHCl_3}$cm$^{-1}$): 3540, 3420 (NH$_2$), 1680 (C=O).

MS(m/e): 282 (M+).

EXAMPLE 49

2-(5,6-dihydro-6-oxo benzo[b]pyrido[3,2-f]oxepin-9-yl)-propionic acid

The mixture of 40 mg of 2-(5,6-dihydro-6-oxo benzo[b]-pyrido[3,2-f]oxepin-9-yl)-propionamide, 180 mg of potassium hydroxide, 1.5 ml of water and 5 ml of ethanol was refluxed with stirring for 5 hours. After cooling, the solvent was distilled off to obtain the residue, to this was added ice-water and the mixture was acidified with acetic acid and extracted with chloroform. The extract was washed with saturated sodium chloride solution and dried over anhydrous sodium sulfate. The solvent was distilled off to obtain the oil, which was chromatographed over silica gel, eluted with chloroform-ethanol, and there was obtained 20 mg of 2-(5,6-dihydro-6-oxo benzo[b]pyrido[3,2-f]oxepin-9-yl)-propionic acid as pale yellow powder.

IR($\nu_{max}^{KBr}$cm$^{-1}$): 1710, 1680 (C=O).

MS(m/e): 283 (M+).

What is claimed as new and intended to be covered by Letters Patent is:

1. A compound of the formula,

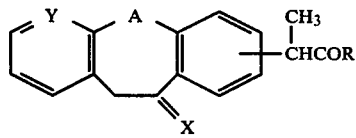

wherein X represents an oxygen or two hydrogen atoms, Y represents CH or N, A represents an oxygen or sulfur atom, and R represents hydroxy, amino or a lower alkoxy group having 1 to 5 carbon atoms.

2. A compound of the formula,

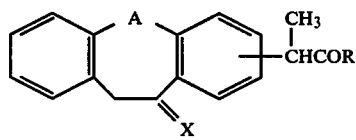

wherein X represents an oxygen or two hydrogen atoms, A represents an oxygen or sulfur atom, and R represents hydroxy, amino or a lower alkoxy group having 1 to 5 carbon atoms.

3. A compound of the formula,

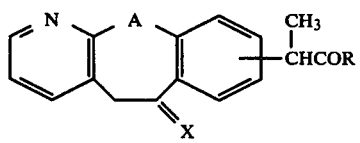

wherein X represents an oxygen or two hydrogen atoms, A represents an oxygen or sulfur atom, and R represents hydroxy, amino or a lower alkoxy group having 1 to 5 carbon atoms.

4. A compound of the formula,

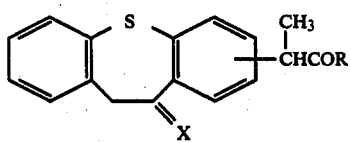

wherein X represents an oxygen or two hydrogen atoms, and R represents hydroxy, amino or a lower alkoxy group having 1 to 5 carbon atoms.

5. A compound of the formula,

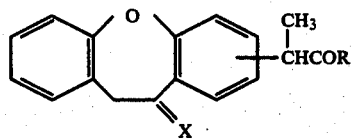

wherein X represents an oxygen or two hydrogen atoms, and R represents hydroxy, amino or a lower alkoxy group having 1 to 5 carbon atoms.

6. A compound of the formula,

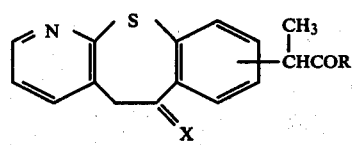

wherein X represents an oxygen or two hydrogen atoms, and R represents hydroxy, amino or a lower alkoxy group having 1 to 5 carbon atoms.

7. A compound of the formula,

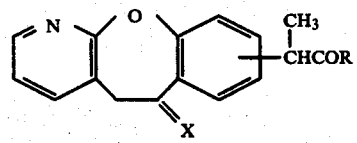

wherein X represents an oxygen or two hydrogen atoms, and R represents hydroxy, amino or a lower alkoxy group having 1 to 5 carbon atoms.

8. A compound of the formula,

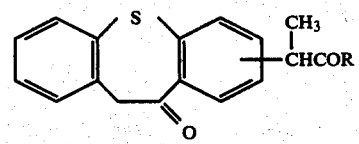

wherein R represents hydroxy, amino or a lower alkoxy group having 1 to 5 carbon atoms.

9. A compound of the formula,

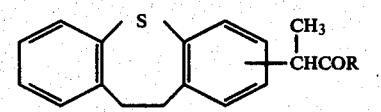

wherein R represents hydroxy, amino or a lower alkoxy group having 1 to 5 carbon atoms.

10. A compound of the formula,

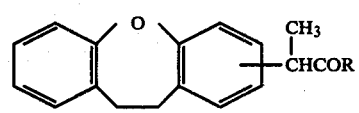

wherein R represents hydroxy, amino or a lower alkoxy group having 1 to 5 carbon atoms.

11. A compound of the formula,

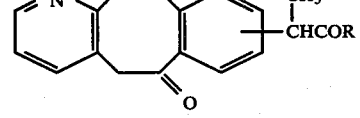

wherein R represents hydroxy, amino or a lower alkoxy group having 1 to 5 carbon atoms.

12. A compound of the formula,

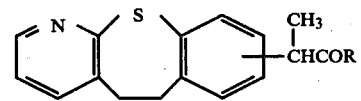

wherein R represents hydroxy, amino or a lower alkoxy group having 1 to 5 carbon atoms.

13. A compound of the formula,

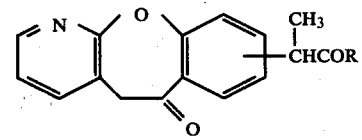

wherein R represents hydroxy, amino or a lower alkoxy group having 1 to 5 carbon atoms.

14. A compound of the formula,

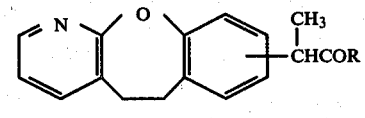

wherein R represents hydroxy, amino or a lower alkoxy group having 1 to 5 carbon atoms.

15. A compound of the formula,

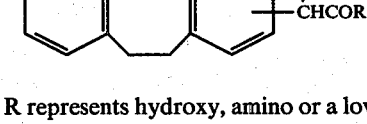

wherein R represents hydroxy, amino or a lower alkoxy group having 1 to 5 carbon atoms.

16. A compound according to claim 8, of the formula,

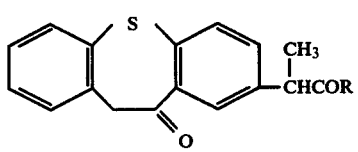

17. A compound according to claim 8, of the formula,

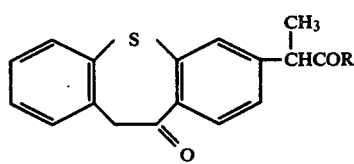

18. A compound according to claim 9, of the formula,

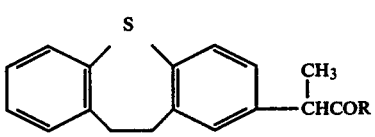

19. A compound according to claim 9, of the formula,

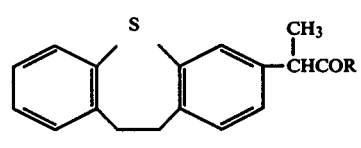

20. A compound according to claim 10, of the formula,

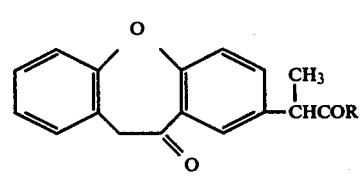

21. A compound according to claim 10, of the formula,

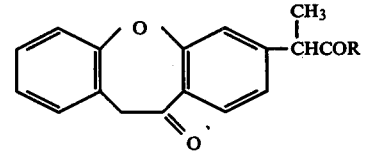

22. A compound according to claim 10, of the formula,

23. A compound according to claim 11, of the formula,

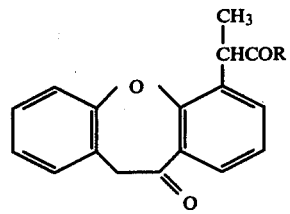

24. A compound according to claim 11, of the formula,

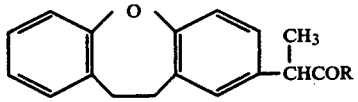

25. A compound according to claim 11, of the formula,

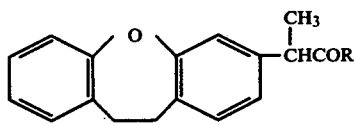

26. A compound according to claim 12, of the formula,

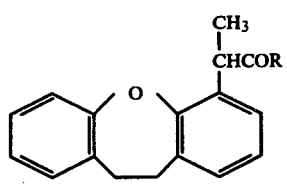

27. A compound according to claim 12, of the formula,

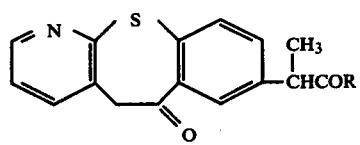

28. A compound according to claim 13, of the formula,

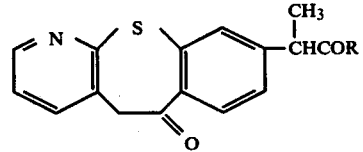

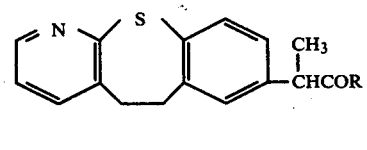

29. A compound according to claim 13, of the formula,

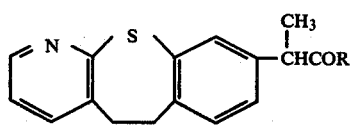

30. A compound according to claim 14, of the formula,

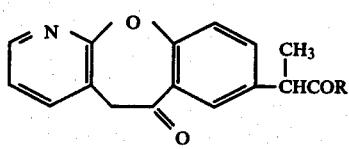

31. A compound according to claim 14, of the formula,

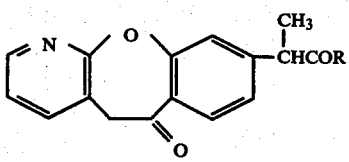

32. A compound according to claim 15, of the formula,

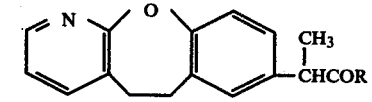

33. 2-(10,11-dihydro-11-oxodibenzo[b,f]thiepin-2-yl)-propionic acid
34. 2-(10,11-dihydro-11-oxodibenzo[b,f]thiepin-2-yl)-propionamide
35. 1-5c lower alkyl 2-(10,11-dihydro-11-oxodibenzo[b,f]-thiepin-2-yl)-propionate
36. 2-(10,11-dihydro-11-oxodibenzo[b,f]oxepin-2-yl)-propionic acid
37. 2-(10,11-dihydro-11-oxodibenzo[b,f]oxepin-2-yl)-propionamide
38. 1-5c lower alkyl 2-(10,11-dihydro-11-oxodibenzo[b,f]-oxepin-2-yl)-propionate
39. 2-(5,6-dihydrobenzo[b]pyrido[3,2-f]thiepin-8-yl)-propionic acid
40. 2-(5,6-dihydrobenzo[b]pyrido[3,2-f]thiepin-8-yl)-propionamide
41. 1-5c lower alkyl 2-(5,6-dihydrobenzo[b]pyrido[3,2-f]-thiepin-8-yl)-propionate
42. 2-(5,6-dihydrobenzo[b]pyrido[3,2-f]oxepin-8-yl)-propionic acid
43. 2-(5,6-dihydrobenzo[b]pyrido[3,2-f]oxepin-8-yl)-propionamide
44. 1-5c lower alkyl 2-(5,6-dihydrobenzo[b]pyrido[3,2-f]-oxepin-8-yl)-propionate

* * * * *